US012605848B2

(12) United States Patent
Taniguchi et al.

(10) Patent No.: US 12,605,848 B2
(45) Date of Patent: Apr. 21, 2026

(54) CRITICAL CARE SYSTEM, CRITICAL CARE SYSTEM CONTROL METHOD, TRANSPORTATION MEANS DETERMINATION SYSTEM, TRANSPORTATION MEANS DETERMINATION METHOD, AND NON-TRANSITORY COMPUTER-READABLE RECORDING MEDIUM RECORDING PROGRAM

(71) Applicant: Honda Motor Co., Ltd., Tokyo (JP)

(72) Inventors: Yoichi Taniguchi, Saitama (JP);
Masaaki Muromachi, Saitama (JP);
Takahide Yoshiike, Saitama (JP);
Kenichiro Sugiyama, Saitama (JP);
Yuta Kimura, Saitama (JP); Tomohiro Kawakami, Saitama (JP)

(73) Assignee: Honda Motor Co., Ltd., Tokyo (JP)

( * ) Notice: Subject to any disclaimer, the term of this patent is extended or adjusted under 35 U.S.C. 154(b) by 757 days.

(21) Appl. No.: 17/717,146

(22) Filed: Apr. 11, 2022

(65) Prior Publication Data

US 2022/0331973 A1     Oct. 20, 2022

(30) Foreign Application Priority Data

Apr. 15, 2021     (JP) ................................. 2021-069010
Apr. 15, 2021     (JP) ................................. 2021-069011
(Continued)

(51) Int. Cl.
*B25J 11/00*       (2006.01)
*B25J 5/00*        (2006.01)
(Continued)

(52) U.S. Cl.
CPC ........... *B25J 11/009* (2013.01); *B25J 9/1689* (2013.01); *G16H 40/63* (2018.01); *B25J 5/00* (2013.01);
(Continued)

(58) Field of Classification Search
CPC . B25J 11/009; B25J 9/1689; B25J 5/00; B25J 5/007; B25J 9/16; B25J 11/00;
(Continued)

(56) References Cited

U.S. PATENT DOCUMENTS

2018/0236666 A1     8/2018  Mozeika et al.
2019/0200844 A1*    7/2019  Shelton, IV .......... H04L 63/123
2023/0134949 A1*    5/2023  Hashimoto .......... B25J 15/0491
                                                    606/1

FOREIGN PATENT DOCUMENTS

CN          204658433          9/2015
CN          111482972          8/2020
(Continued)

OTHER PUBLICATIONS

"Office Action of Japan Counterpart Application", issued on Jun. 25, 2024, with English translation thereof, p. 1-p. 8.
(Continued)

*Primary Examiner* — Basil T. Jos
(74) *Attorney, Agent, or Firm* — JCIPRNET

(57)                    ABSTRACT

The disclosure provides a critical care system, a critical care system control method, and a non-transitory computer-readable recording medium recording a program. A critical care system includes: a photographing device which is capable of remotely controlling at least one of a position and a direction; a critical care tool storage part which stores a critical care tool; a critical care robot which includes at least one end effector that allows for remote control; a terminal with which at least one operator remotely operates the
(Continued)

critical care robot; and a server which is capable of acquiring medical condition information and environmental information acquired by the critical care robot, transmitting the acquired medical condition information and environmental information to the terminal, receiving operation information for the critical care robot from the terminal, and controlling the critical care robot based on the received operation information.

15 Claims, 26 Drawing Sheets

(30)     Foreign Application Priority Data

| Apr. 15, 2021 | (JP) | ................................. | 2021-069012 |
| Apr. 15, 2021 | (JP) | ................................. | 2021-069013 |
| Apr. 15, 2021 | (JP) | ................................. | 2021-069014 |

(51)  Int. Cl.

| *B25J 9/16* | (2006.01) |
| *G05D 1/00* | (2024.01) |
| *G16H 40/63* | (2018.01) |

(52)  U.S. Cl.
CPC .. *G05B 2219/45117* (2013.01); *G05D 1/0212* (2013.01)

(58)  Field of Classification Search
CPC ......... B25J 19/00; G16H 40/63; G16H 15/00; G16H 20/00; G16H 30/20; G16H 40/20; G16H 40/67; G16H 10/60; G16H 50/30; G16H 80/00; G05B 2219/45117; G05B 2219/40411; G05D 1/0212
See application file for complete search history.

(56)     References Cited

FOREIGN PATENT DOCUMENTS

| CN | 111687855 | 9/2020 |
| JP | 2002007579 | 1/2002 |
| JP | 2002042291 | 2/2002 |
| JP | 2006326229 | 12/2006 |
| JP | 2006338081 | 12/2006 |
| JP | 2009224967 | 10/2009 |
| JP | 2011143511 | 7/2011 |
| JP | 2014211704 | 11/2014 |
| JP | 5705621 | 4/2015 |
| JP | 2017138699 | 8/2017 |

OTHER PUBLICATIONS

"Office Action of Japan Counterpart Application", issued on Jun. 25, 2024, with English translation thereof, p. 1-p. 6.
"Notice of Reasons for Refusal of Japan Counterpart Application", issued on Jan. 21, 2025, with English translation thereof, p. 1-p. 6.

* cited by examiner

| Mobile phone number | Full name | Medical history | Emergency contact | Family surgery | |
|---|---|---|---|---|---|
| 080-XXXX-XXXX | Ito XXX | High blood pressure | 03-AAAA-BBBB | ○□ Hospital | ⋮ |
| 080-XXXX-XXXA | Sato XXX | Diabetes | ⋮ | △ Clinic | ⋮ |
| 080-XXXX-XXXB | Murata XXX | Heart disease | ⋮ | ⋮ | ⋮ |
| ⋮ | ⋮ | ⋮ | ⋮ | ⋮ | ⋮ |

FIG. 5

| Priority |
|----------|
| Assistant critical care technician |
| Critical care technician |
| . . . |
| . . . | g121 g122

2A

CRITICAL CARE SYSTEM, CRITICAL CARE SYSTEM CONTROL METHOD, TRANSPORTATION MEANS DETERMINATION SYSTEM, TRANSPORTATION MEANS DETERMINATION METHOD, AND NON-TRANSITORY COMPUTER-READABLE RECORDING MEDIUM RECORDING PROGRAM

CROSS-REFERENCE TO RELATED APPLICATION

This application claims the priority benefit of Japan application serial no. 2021-069010, filed on Apr. 15, 2021; Japan application serial no. 2021-069011, filed on Apr. 15, 2021; Japan application serial no. 2021-069012, filed on Apr. 15, 2021; Japan application serial no. 2021-069013, filed on Apr. 15, 2021; and Japan application serial no. 2021-069014, filed on Apr. 15, 2021. The entirety of each of the above-mentioned patent applications is hereby incorporated by reference herein and made a part of this specification.

BACKGROUND

Technical Field

The disclosure relates to a critical care system, a critical care system control method, and a non-transitory computer-readable recording medium recording a program.

Related Art

There is a demand for a system capable of carrying a device that automatically monitors and transmits biometric information of a user, determining the degree of abnormality in physical condition, notifying a third party as necessary, and requesting a critical care. As such a system, a critical care assistance system has been proposed that uses a telephone or the Internet to assist the critical care to determine and notify the degree of abnormality of the user's physical condition based on the user's biometric information acquired by the mobile terminal carried by the user (see, for example, Patent Literature 1).

In the critical care assistance system described in Patent Literature 1, the user terminal device includes a biometric information detection part that detects the biometric information of the user, a user terminal position detection part that measures the user position information indicating the position of the user terminal device, and a critical care information communication part that transmits critical care information including biometric information and user position information to a critical care assistance device. In addition, a third party terminal device includes a third party terminal position detection part that measures the position information of the third party terminal device, and a third party terminal critical care information transmission and reception part that periodically transmits third party terminal information including the third party terminal position information of the third party terminal device to the critical care assistance device and receives critical care instruction information from the critical care assistance device. In addition, the critical care assistance device includes a critical care information transmission and reception part that receives critical care information and third party terminal information and transmits critical care instruction information to the third party terminal device; an urgent determination part that determines the urgency of the critical care from the critical care information and outputs the urgency information; a position information analysis part that analyzes the positional relationship of the third party near the user's current position based on the critical care information and the third party terminal position information and outputs distance information between the user terminal device and the third party terminal device; a database that records a history of biometric information of the user, distance information, and attribute information of the third party in correspondence with a plurality of third party terminal devices; and a notifier determination part that identifies a third party terminal device that transmits the critical care instruction information by inputting urgency information, distance information, and attribute information of the third party.

A critical care assistance system has been proposed that assists in critical care to determine and notify the degree of abnormality in the user's physical condition based on the biometric information of the user acquired by the mobile terminal carried by the user (for example, see Patent Literature 1). In the technique described in Patent Literature 1, a mobile phone owned by a user is used. In addition, there is also a method in which the rescue team and the like communicate with a bystander (a person who was present at the critical care site) by video telephone and the like at the time of critical care. For example, in the technique described in Patent Literature 1, for example, when the third party terminal has a video telephone function, the critical care assistance device side can make a video call to the third party terminal.

A remotely controllable robot system has been proposed that enables critical care treatment and prompt delivery of patients to the medical side in areas remote from places such as critical care medical centers where medical treatment is possible (See, for example, Patent Literature 2). In the robot device described in Patent Literature 2, a person near the robot device travels and meanders the robot device to move the robot device to a place where a patient is present. Further, the robot system described in Patent Literature 1 includes a robot remote control device main body that generates and transmits control data, an image and voice remote control device that transmits and receives image data and voice data, and biometric information remote control device that receives biometric information.

In recent years, automated external defibrillators (AEDs) have been installed in various places. AEDs can be used by the general public, even if they are not specialists like critical care technicians. For this reason, there are an increasing number of cases in which the general public uses AEDs to rescue patients. Since the place where the AED is installed is limited, the location of the AED is unknown, and it takes time to find the AED, and life may be lost. For this reason, a system has been proposed in which a reporter who encounters a suddenly ill person and dials "119" is asked about the condition of the suddenly ill person, and when an AED is required, the AED position information is transmitted to the reporter (for example, see Patent Literature 3).

A traffic signal control device has been proposed that enables critical care vehicles to reach their destinations faster and more safely, suppresses the occurrence of traffic congestion as much as possible, and balances the two (see, for example, Patent Literature 4).

In addition, a critical care system has been proposed that can more accurately determine the necessity of transporting the subject (see, for example, Patent Literature 5).

The traffic signal control device described in Patent Literature 4 includes a reception part that receives vehicle information transmitted from the emergency vehicle, a recognition part that recognizes the type of the emergency vehicle based on the vehicle information received by the reception part, a setting part that sets a time for controlling the display of the traffic signal based on the type of the emergency vehicle recognized by the recognition part, and a control part that controls the display of the traffic signal according to the time set by the setting part.

The critical care system described in Patent Literature 5 includes a first display control part that displays a screen for selecting one or more symptom items from a plurality of predetermined symptom items; a first storage that stores question contents set for each of the symptom items and including a quantitative question asking the amount, a qualitative question asking the nature, and a time question asking the time of the symptom indicated by each symptom item; a second display control part for reading the question contents of the quantitative question, the qualitative question, and the time question set in the selected symptom item on the screen displayed by the first display control part from the first storage part and sequentially displaying them on the screen; a symptom result determination part that determines the result for each symptom according to the answer result to the question content of each symptom item input sequentially on the screen displayed sequentially by the second display control part; and a transportation determination part for determining whether the subject needs to be transported based on the result for each symptom determined by the symptom result determination part.

CITATION LIST

Patent Literature

[Patent Literature 1] Japanese Patent Publication No. 5705621

[Patent Literature 2] Japanese Patent Lain-Open No. 2006-326229

[Patent Literature 3] Japanese Patent Laid-Open No. 2009-224967

[Patent Literature 4] Japanese Patent Laid-Open No. 2002-042291

[Patent Literature 5] Japanese Patent Laid-Open No. 2017-138699

However, in the critical care assistance system described in Patent Literature 1, it is the person near the site who actually performs the critical care, and it is not always the case that a critical care technician will come, and there is a limit to what can be done with words and images displayed on the monitor. Also, with video telephones, it is difficult to give instructions on what action to take. In addition, video telephones cannot handle cases where the cooperation of multiple people is required or the number of people in a panic is large. In addition, depending on the treatment, it may be necessary to undress the clothes of the suddenly ill person, so it may not be possible to protect the privacy of the suddenly ill person.

Further, the robot device described in Patent Literature 2 is large in size, and it is difficult to install a large number of robot devices in various places, like the AEDs. Further, In the robot system described in Patent Literature 1, in order to acquire biometric information, it is necessary to seat the patient on the seat of the robot device on the site. However, depending on the patient's condition, sometimes the patient should not be moved. Therefore, in the technique described in Patent Literature 1, it may be necessary to assign a person who can perform medical treatment not only to remote control but also to the site.

However, in the system described in Patent Literature 3, the reporter needs to go to get the AED, and it takes time to make a round trip from the position of the suddenly ill person to the position of the AED and from the position of the AED to the position of the suddenly ill person.

In the conventional technique, it may not be possible to calmly select the means of transportation from the options in the event of an emergency.

The disclosure has been made in view of the above-mentioned problems, and it is possible to provide a critical care system, a critical care system control method, and a non-transitory computer-readable recording medium recording a program, with which it is possible to provide rescue by remote control even if on the site there is no person who can perform medical treatment, and it is possible for a person near the critical care device to carry it to the position of the patient without the reporter having to go to the critical care device.

The disclosure provides a transportation means determination system, a transportation means determination method, and a non-transitory computer-readable recording medium recording a program capable of selecting a transportation means from options in an emergency.

The disclosure provides a critical care system, a critical care robot, a critical care system control method, and a non-transitory computer-readable recording medium recording a program capable of ensuring the safety of the site and protecting privacy.

SUMMARY (1) In view of the above, a critical care system according to an embodiment of the disclosure includes: a photographing device which is capable of remotely controlling at least one of a position and a direction; a critical care tool storage part which stores a critical care tool; a critical care robot which includes at least one end effector that allows for remote control; a terminal with which at least one operator remotely operates the critical care robot; and a server which is capable of acquiring medical condition information and environmental information acquired by the critical care robot, transmitting the acquired medical condition information and environmental information to the terminal, receiving operation information for the critical care robot from the terminal, and controlling the critical care robot based on the received operation information.

(6) In view of the above, a critical care system control method for a critical care system according to an embodiment of the disclosure is provided. The critical care system includes a photographing device which is capable of remotely controlling at least one of a position and a direction, a critical care tool storage part which stores a critical care tool, a critical care robot which includes at least one end effector that allows for remote control, a terminal with which at least one operator remotely operates the critical care robot, and a server. The critical care system control method includes: acquiring, by the critical care robot, medical condition information and environmental information, and transmitting the acquired medical condition information and environmental information to the server; and transmitting, by the server, the acquired medical condition information and environmental information to the terminal, receiving operation information for the critical care robot from the terminal, and controlling the critical care robot based on the received operation information.

(7) In view of the above, a non-transitory computer-readable recording medium recording a program for a critical care system according to an embodiment of the disclosure is provided. The critical care system includes a photographing device capable of remotely controlling at least one of a position and a direction, a critical care tool storage part which stores a critical care tool, a critical care robot which includes at least one end effector that allows for remote control, a terminal with which at least one operator remotely operates the critical care robot, and a server. The program causes a computer of the server to: acquire, by the critical care robot, medical condition information and environmental information, and transmit the acquired medical condition information and environmental information to the server; transmit the acquired medical condition information and the environmental information to the terminal; and receive operation information for the critical care robot from the terminal, and control the critical care robot based on the received operation information.

(8) In view of the above, a critical care robot which allows for remote control according to an embodiment of the disclosure is provided. The critical care robot includes: a photographing device which is capable of remotely controlling at least one of a position and a direction; a critical care tool storage part which stores a critical care tool; and at least one end effector which allows for remote control.

(16) In view of the above, a critical care robot system according to an embodiment of the disclosure includes the critical care robot according to any of the above (8) to (15); at least one terminal used for remote control of the critical care robot; a position information acquisition device which acquires position information of a patient to receive critical care; and a server which generates control information for the critical care robot based on remote control from the terminal.

(17) In view of the above, a critical care system according to an embodiment of the disclosure includes a critical care device; and a critical care reporting device which issues a critical care report. The critical care device includes: at least one end effector which allows for remote control; a route generation part which generates route information from a self-position to a position where the critical care report is issued based on a difference between position information where the critical care report is issued and the self-position of the critical care device; and an output part which notifies a person around the critical care device by using at least one of a sound and an image for navigation from the self-position to the position where the critical care report is issued based on the route information generated by the route generation part.

(21) In view of the above, a critical care method using a critical care system according to an embodiment of the disclosure is provided. The critical care system includes a critical care device and a critical care reporting device which issues a critical care report, and the critical care device includes at least one end effector which allows for remote control and a route generation part. The critical care method includes: generating, by the route generation, route information from a self-position to a position where the critical care report is issued based on a difference between position information where the critical care report is issued and the self-position of the critical care device; and notifying, by an output part, a person around the critical care device by using at least one of a sound and an image for navigation from the self-position to the position where the critical care report is issued based on the route information generated by the route generation part.

(22) In view of the above, a non-transitory computer-readable recording medium recording a program which causes a computer to execute a critical care method using a critical care system according to an embodiment of the disclosure is provided. The critical care system includes a critical care device and a critical care reporting device which issues a critical care report, and the critical care device includes at least one end effector which allows for remote control and a route generation part. The program causes the computer to: generate route information from a self-position to a position where the critical care report is issued based on a difference between position information where the critical care report is issued and the self-position of the critical care device; and notify a person around the critical care device by using at least one of a sound and an image for navigation from the self-position to the position where the critical care report is issued based on the generated route information.

(23) In view of the above, a transportation means determination system according to an embodiment of the disclosure includes a critical care device which includes at least one end effector that allows for remote control and which is capable of acquiring medical condition information and environmental information; a server which acquires the environmental information and the medical condition information acquired from the critical care device; a terminal which is capable of acquiring the medical condition information and the environmental information, which is capable of remotely controlling the critical care device, and which transmits a determination result determined based on the acquired medical condition information and the environmental information to the server; and a transportation means determination part which determines at least one transportation means from a plurality of transportation means using at least one information of the medical condition information, the environmental information, and the determination result.

(28) In view of the above, a transportation means determination method according to an embodiment of the disclosure includes: acquiring, by a critical care device which includes at least one end effector that allows for remote control, medical condition information and environmental information; acquiring, by a server, the environmental information and the medical condition information acquired from the critical care device; transmitting, by a terminal which is capable of acquiring the medical condition information and the environmental information and which is capable of remotely controlling the critical care device, a determination result determined based on the acquired medical condition information and the environmental information to the server; and determining, by a transportation means determination part, at least one transportation means from a plurality of transportation means using at least one information of the medical condition information, the environmental information, and the determination result.

(29) In view of the above, a non-transitory computer-readable recording medium recording a program according to an embodiment of the disclosure is provided. The program causes a computer to: acquire, from a critical care device which has acquired medical condition information and environmental information and which includes at least one end effector that allows for remote control, the medical condition information and the environmental information; transmit, by a terminal which is capable of acquiring the medical condition information and the environmental information and which is capable of remotely controlling the critical care device, a determination result determined based on the acquired medical condition information and the environmental information; acquire a determination result determined based on the acquired medical condition information and the environmental information by the terminal which is capable of remotely controlling the critical care device and which is capable of acquiring the medical condition information and the environmental information; and determine at least one transportation means from a plurality of transportation means using at least one information of the medical condition information, the environmental information, and the determination result.

(30) In view of the above, a critical care system according to an embodiment of the disclosure includes a critical care device which includes a remote control function by at least one end effector that allows for remote control, a photographing device that acquires environmental information around a patient, and a plurality of notification parts; a terminal which acquires the environmental information and transmits selection information indicating a bystander selected by using the acquired environmental information; and a directivity operation part which adjusts a directivity to the selected bystander based on the selection information acquired from the terminal and controls a directivity of at least one of the plurality of the notification parts to the bystander.

(35) In view of the above, a critical care robot according to an embodiment of the disclosure includes a remote control function by at least one end effector which allows for remote control; a photographing device which acquires environmental information around a patient; a plurality of notification parts; and a directivity operation part which, based on selection information acquired from a terminal which acquires the environmental information and transmits the selection information indicating a bystander selected by using the acquired environmental information, adjusts a directivity to the selected bystander and controls a directivity of at least one of the plurality of the notification parts to the bystander.

(36) In view of the above, a critical care system control method according to an embodiment of the disclosure includes acquiring, by a photographing device, environmental information around a patient by causing the photographing device to photograph an image; transmitting, by a terminal, selection information indicating a bystander selected by using the acquired environmental information; and adjusting, by a directivity operation part, a directivity to the selected bystander based on the selection information acquired from the terminal and controlling a directivity of at least one of a plurality of notification parts to the bystander.

(37) In view of the above, a non-transitory computer-readable recording medium recording a program according to an embodiment of the disclosure is provided. The program causes a computer to: acquire environmental information around a patient by causing a photographing device to photograph an image; and based on selection information indicating a bystander selected by using the acquired environmental information, adjust a directivity to the selected bystander and control a directivity of at least one of a plurality of notification parts to the bystander.

BRIEF DESCRIPTION OF THE DRAWINGS

FIG. 5 is a diagram showing an example of data stored in a database according to an embodiment.

Figure 1:
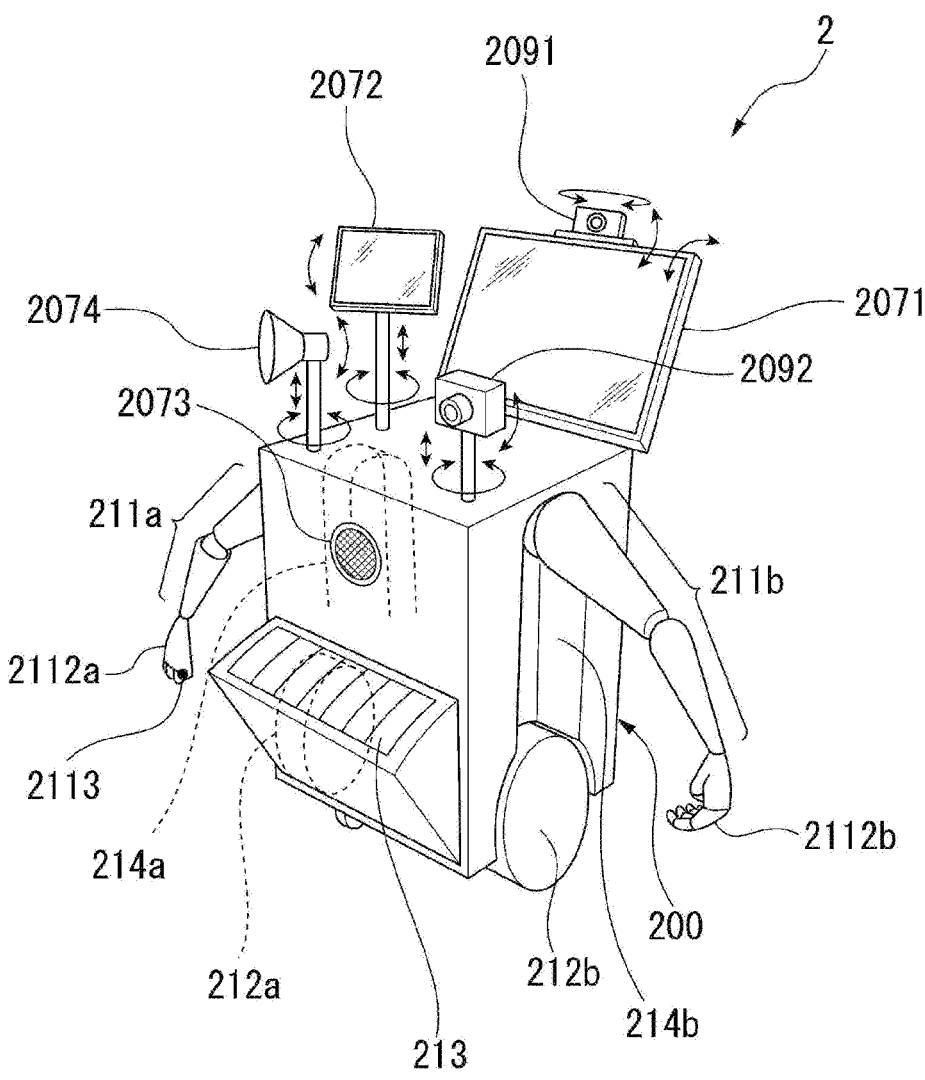
FIG. 1 is a diagram showing a configuration example of a critical care robot according to an embodiment.

DESCRIPTION OF THE EMBODIMENTS (2) Further, in the critical care system according to an embodiment of the disclosure, the critical care robot may be capable of being operated by a plurality of people, and the server may transfer a control right of an operator having a low priority to an operator having a high priority based on a priority.

(3) Further, in the critical care system according to an embodiment of the disclosure, there may be a plurality of the terminals, and a first terminal may be operated by an operator of the critical care robot, and a second terminal may be operated by a doctor; the critical care robot may include a photographing device; and the photographing device may be operable by the doctor by operating the second terminal, and may be capable of observing a patient from a different viewpoint from the operator of the critical care robot.

(4) Further, in the critical care system according to an embodiment of the disclosure, there may be a plurality of the terminals, and a coordinator may operate another terminal different from a terminal operated by an operator of the critical care robot; and the another terminal may transmit a result of determining a destination hospital based on medical condition information and environmental data by the coordinator to the server.

(5) Further, in the critical care system according to an embodiment of the disclosure, the server may transmit the medical condition information acquired by the critical care robot to the terminal in real time, and add a processing instruction to environmental data acquired by the critical care robot at the time of storage for privacy protection.

(9) Further, in the critical care robot according to an embodiment of the disclosure, the end effector may include a pointer, and the pointer may instruct a person who performs a treatment on a patient to be treated by the remote control.

(10) Further, in the critical care robot according to an embodiment of the disclosure, two arms may be further included, and the end effector may be capable of operating the critical care tool and may be connected to the two arms.

(11) Further, in the critical care robot according to an embodiment of the disclosure, a photographing device which is connectable by another person in addition to a main remote operator may be further included.

(12) Further, in the critical care robot according to an embodiment of the disclosure, a plurality of display devices and speakers with directivity may be further included.

(13) Further, in the critical care robot according to an embodiment of the disclosure, a movement means may be further included.

(14) Further, in the critical care robot according to an embodiment of the disclosure, the movement means may be driven to assist movement when the critical care robot is moving.

(15) Further, in the critical care robot according to an embodiment of the disclosure, the end effector may be storable in a main body.

(18) Further, in the critical care system according to an embodiment of the disclosure, the output part may be at least one of a display device and a speaker with directivity.

(19) Further, in the critical care system according to an embodiment of the disclosure, the critical care device may include a movement means which assists in movement from the self-position to the position where the critical care report is issued.

(20) Further, in the critical care system according to an embodiment of the disclosure, the route generation part may generate a route from the position where the critical care report is issued to the self-position using a priority different from a route from the self-position to the position where the critical care report is issued.

(24) Further, in the transportation means determination system according to an embodiment of the disclosure, when the transportation means determination part determines the transportation means, the transportation means determination part may transmit the medical condition information to a transportation destination according to the determined transportation means.

(25) Further, in the transportation means determination system according to an embodiment of the disclosure, when the transportation means determination part determines the transportation means, the transportation means determination part may generate and transmit traffic control information of a transportation route according to the determined transportation means.

(26) Further, in the transportation means determination system according to an embodiment of the disclosure, the medical condition information may be at least one of a patient's medical history, respiratory status, pulse rate, blood pressure, body temperature, consciousness level, and degree of bleeding; and the environmental information may be at least one of the number of people around the patient, ground and topography related information, and a surrounding traffic volume.

(27) Further, in the transportation means determination system according to an embodiment of the disclosure, the transportation means determination part may be provided in the server or the critical care device.

(31) Further, in the critical care system according to an embodiment of the disclosure, the notification part may be at least one of a speaker and an image display part.

(32) Further, in the critical care system according to an embodiment of the disclosure, the number of the speakers may be two, and the directivity operation part controls the directivity by controlling left and right phases of notified audio signals.

(33) Further, in the critical care system according to an embodiment of the disclosure, a support determination part may be further included. The support determination part determines whether a support request to another critical care device is necessary and issues the support request to the another critical care device when determining that the support request is necessary.

(34) Further, in the critical care system according to an embodiment of the disclosure, the another critical care device may include a movement means; the support request may include route information and navigation information from the another critical care device to the critical care device; and the another critical care device may notify a person around the another critical care device of the route information and the navigation information included in the support request acquired from the directivity operation part.

According to (1) to (7), even if there is no person who can perform medical treatment at the site, since the critical care robot can be remotely controlled to acquire the medical condition information, the rescue can be performed.

According to (2), since one critical care robot can be remotely controlled smoothly and efficiently by a plurality of operators, rescue can be performed efficiently.

According to (3), the doctor can observe the patient from a different viewpoint from the operator of the critical care robot.

According to (4), it is possible to select a transportation means from the options in case of an emergency. According to (4), since the transportation method is expanded in addition to the ambulance, ambulances can reach those who really need them. According to (4), the number of times the ambulance is dispatched can be reduced.

According to (5), the privacy of the patient, the person who treats the patient, and the people around the patient can be protected.

According to (8) to (16), even if there is no person who can perform medical treatment at the site, the rescue can be performed by remote control.

According to (9), it is possible to instruct a person or the like who performs treatment or the like on a patient with a pointer.

According to (10), critical care tools can be operated.

According to (11), a person (for example, a doctor) in addition to the main remote operator can remotely control the photographing device to learn the patient's condition.

According to (12), it is possible to appropriately notify the person to be notified among the surrounding people at the time of treatment.

According to (13) and (14), it becomes easy for the reporter to make the critical care robot move from the installation position. Further, according to (13) and (14), the arrival time is shortened, and more lives can be saved.

According to (15), it can be installed compactly when it is not used for critical care.

According to (17) to (22), even if the reporter does not go to pick up the critical care device, it is possible to have a person near the critical care device carry it to the position where the patient is.

According to (18), it becomes easy to navigate for the person who moves the critical care device.

According (19), it becomes easy for the reporter to make the critical care device move from the installation position.

Further, according to (20), the arrival time is shortened, and more lives can be saved.

According to (23) to (29), it is possible to select a transportation means from the options in case of an emergency. According to (23) to (29), since the transportation method is expanded in addition to the ambulance, ambulances can reach those who really need them. According to (23) to (29), the number of times the ambulance is dispatched can be reduced.

According to (24), the destination hospital can acquire the patient's medical condition information before the patient is transported, and thus can prepare for receiving the patient.

According to (25), traffic control at the time of transporting a patient can be performed according to the transportation means.

According to (30) to (37), it is possible to ensure the safety of the site and protect the privacy.

According to (32), it is possible to notify the target person by controlling the phase of the audio signal output from the speaker.

According to (33) and (34), treatment can be performed using a plurality of critical care robots according to the patient's medical condition and status and the surrounding environment.

According to (36), it is possible to shorten the time for moving the critical care robot used for support to the patient.

Hereinafter, embodiments of the disclosure will be described with reference to the drawings. In the drawings used in the following description, the scale of each member is appropriately changed in order to make each member recognizable.

[Configuration Example of Critical Care Robot]

An example of a critical care robot will be described with reference to FIGS. 1 and 2.

FIG. 1 is a diagram showing a configuration example of a critical care robot according to an embodiment. As shown in FIG. 1, the critical care robot 2 includes, for example, a housing 200, an arm 211a (arm, end effector), an arm 211b (arm, end effector), a first display device 2071, a second display device 2072, a first speaker 2073, a second speaker 2074, a first photographing device 2091, a second photographing device 2092, a movement means 212a, a movement means 212b, a critical care tool storage part 213, an arm storage part 214a, an arm storage part 214b, and the like. The arm 211a includes a hand 2112a. The arm 211b includes a hand 2112b. Further, in the critical care robot 2, for example, a pointer 2113 is attached to a hand 2112 (2112a, 2112b) (end effector). The critical care robot 2 may hold the pointer 2113 with the hand 2112.

Figure 2:
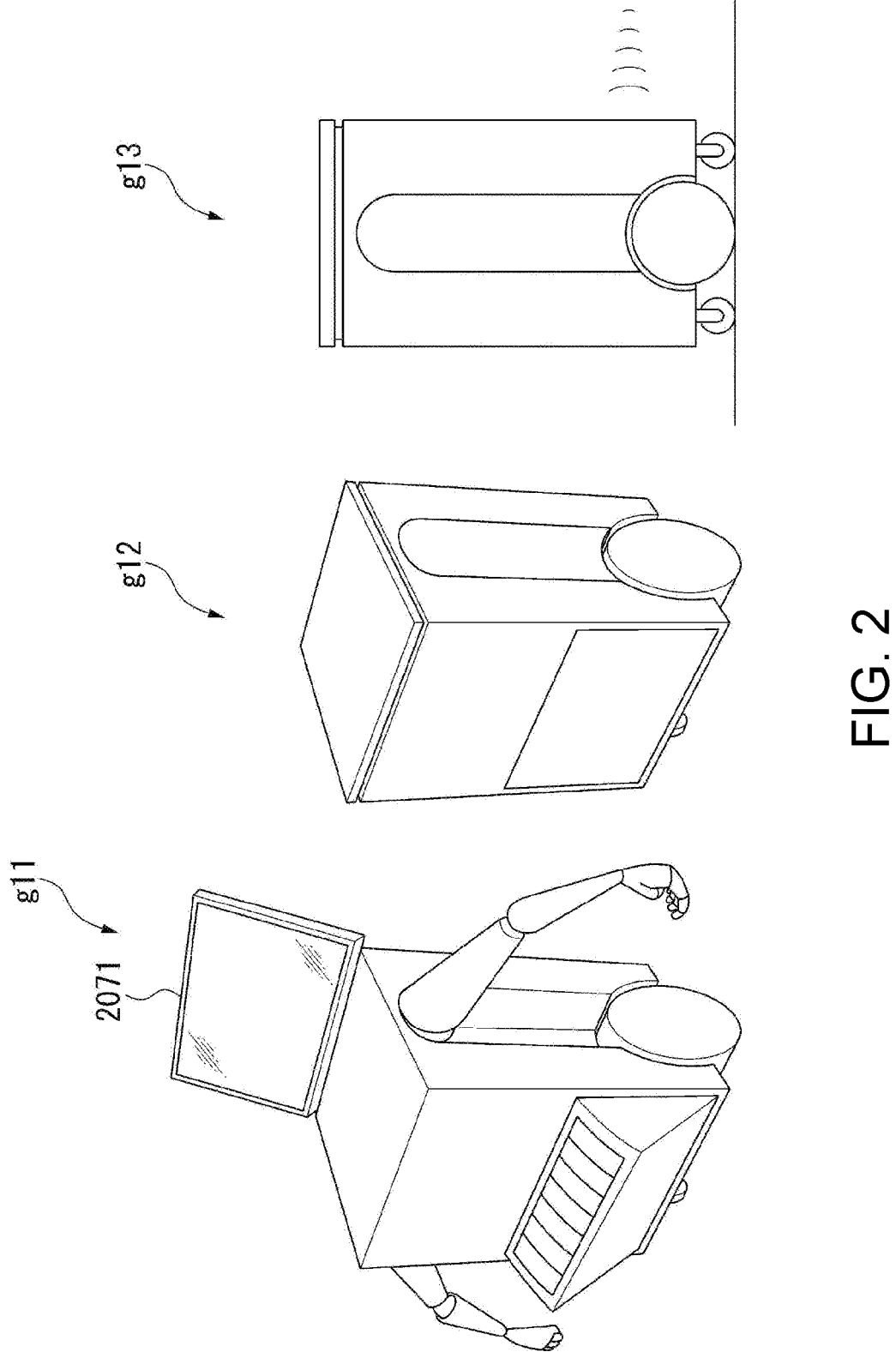
FIG. 2 is a diagram showing an appearance example of a critical care robot according to an embodiment.

FIG. 2 is a diagram showing an appearance example of a critical care robot according to an embodiment. A first appearance g11 is a state in which the arms 211 (211a, 211b) are taken out from the arm storage part 214 (214a, 214b), and the first display device 2071 is in a state in which information can be presented, and the critical care tool storage part 213 is open (or opened) so that the critical care tool (not shown) can be taken out. The critical care tool is, for example, a sphygmomanometer, a pulse measuring device, a body temperature measuring device, a respiratory measuring device, an AED, a mask, a sling, a stethoscope, an airway management device, and the like.

A second appearance g12 is a state in which it is arranged at a predetermined position or place, and the arms 211 are housed in the arm storage part 214, and the first display device 2071 is closed, and the critical care tool storage part 213 is closed and the critical care tool (not shown) cannot be taken out.

A third appearance g13 is a state in which the critical care robot 2 is moving or a state in which the critical care robot 2 is being moved. The critical care robot 2 may be self-propelled and movable, or may be movable by a person.

The appearance of the critical care robot 2 shown in FIGS. 1 and 2 is an example, and the disclosure is not limited thereto.

Figure 3:
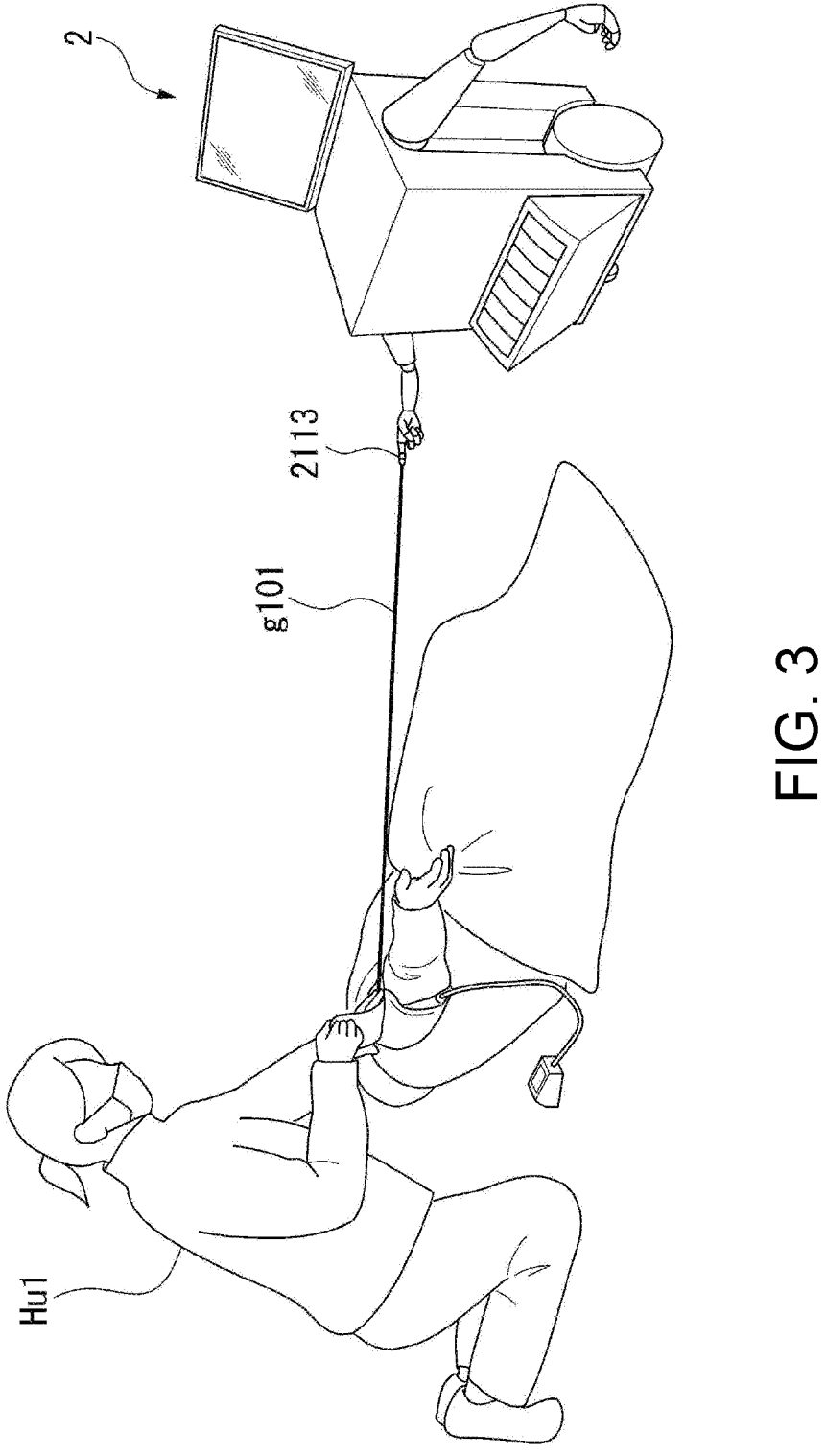
FIG. 3 is a diagram showing an example of a working state of the critical care robot according to the first embodiment at the time of critical care.

In the embodiment, as shown in FIG. 3, the critical care robot 2 does not touch a person such as a patient, but instructs a person Hu1 nearby by, for example, light g101 of the pointer 2113. FIG. 3 is a diagram showing an example of work of the critical care robot according to the embodiment at the time of critical care.

[Configuration Example of Critical Care System]

Figure 4:
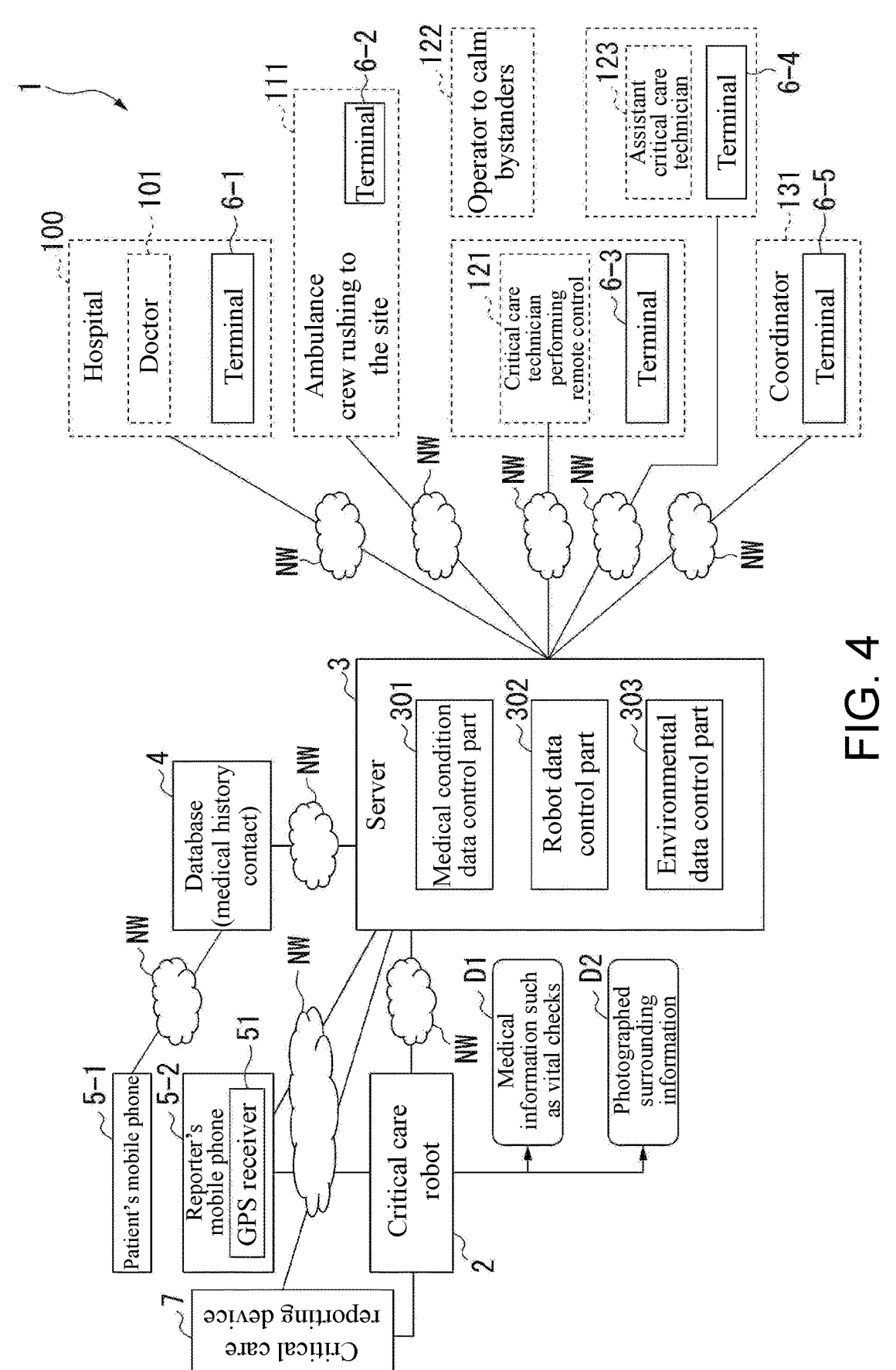
FIG. 4 is a diagram showing a configuration example of a critical care system according to an embodiment.

Next, a configuration example of the critical care system will be described. FIG. 4 is a diagram showing a configuration example of a critical care system according to an embodiment. As shown in FIG. 2, the critical care system 1 includes, for example, the critical care robot 2, a server 3, a database 4, a patient's mobile phone 5-1, a reporter's mobile phone 5-2, a terminal 6-1 used by a doctor 101 and the like in a hospital 100, a terminal 6-2 used by an ambulance crew 111 rushing to the site, a terminal 6-3 used by a critical care technician 121 remotely operating, a terminal 6-4 used by an assistant critical care technician 123, a terminal 6-5 used by a coordinator 131, and the like. The terminal 6 (6-1, 6-2, 6-3, 6-4, 6-5) is, for example, at least one of a smartphone, a tablet terminal, a notebook computer with a communication function, and a dedicated device. The reporter's mobile phone 5-2 is equipped with, for example, a GPS receiver 51.

In the following description, "the patient's mobile phone 5-1" may be referred to as "the mobile phone 5-1"; "the reporter's mobile phone 5-2" may be referred to as "the mobile phone 5-2"; "the terminal 6-1 used by the doctor 101 and the like in the hospital 100" may be referred to as "the terminal 6-1"; "the terminal 6-2 used by the ambulance crew 111 rushing to the site" may be referred to as "the terminal 6-2"; "the terminal 6-3 used by the critical care technician 121 remotely operating" may be referred to as "the terminal 6-3"; "the terminal 6-4 used by the assistant critical care technician 123" may be referred to as "the terminal 6-4"; and "the terminal 6-5 used by the coordinator 131" may be referred to as "the terminal 6-5."

Further, in the following description, "the ambulance crew 111 rushing to the site" may be referred to as "the ambulance crew 111", and the "the critical care technician 121 remotely operating" may be referred to as "the critical care technician 121."

Each mobile phone, each terminal, the critical care robot 2, the server 3, the database 4, and the like are connected to a network NW by, for example, a communication line or an Internet line.

The critical care robot 2 is installed in a place where people gather, such as a shopping center, a station, a public hall, or a museum.

The configuration and functions of the critical care robot 2 and the server 3, the data acquired and transmitted by the critical care robot 2, the person who assists the critical care, and the like will be described in the embodiment.

A critical care reporting device 7 can also be installed, for example, in places where people gather, such as a shopping center, a station, a public hall, or a museum. The critical care reporting device may be a mobile phone or the like used by the reporter.

FIG. 5 is a diagram showing an example of data stored in a database according to an embodiment.

As shown in FIG. 5, the database 4 stores, for example, a mobile phone number in association with information such as a name, medical history, critical care contact information, and a family surgery. The database 4 stores at least a mobile phone number in association with a medical history and contact information. The data stored in the database 4 of FIG. 5 is an example, and the disclosure is not limited thereto. The database 4 may store other information in association with each other.

[Configuration Example of Critical Care Robot]

First, a configuration example of the critical care robot 2 will be described.

Figure 6:
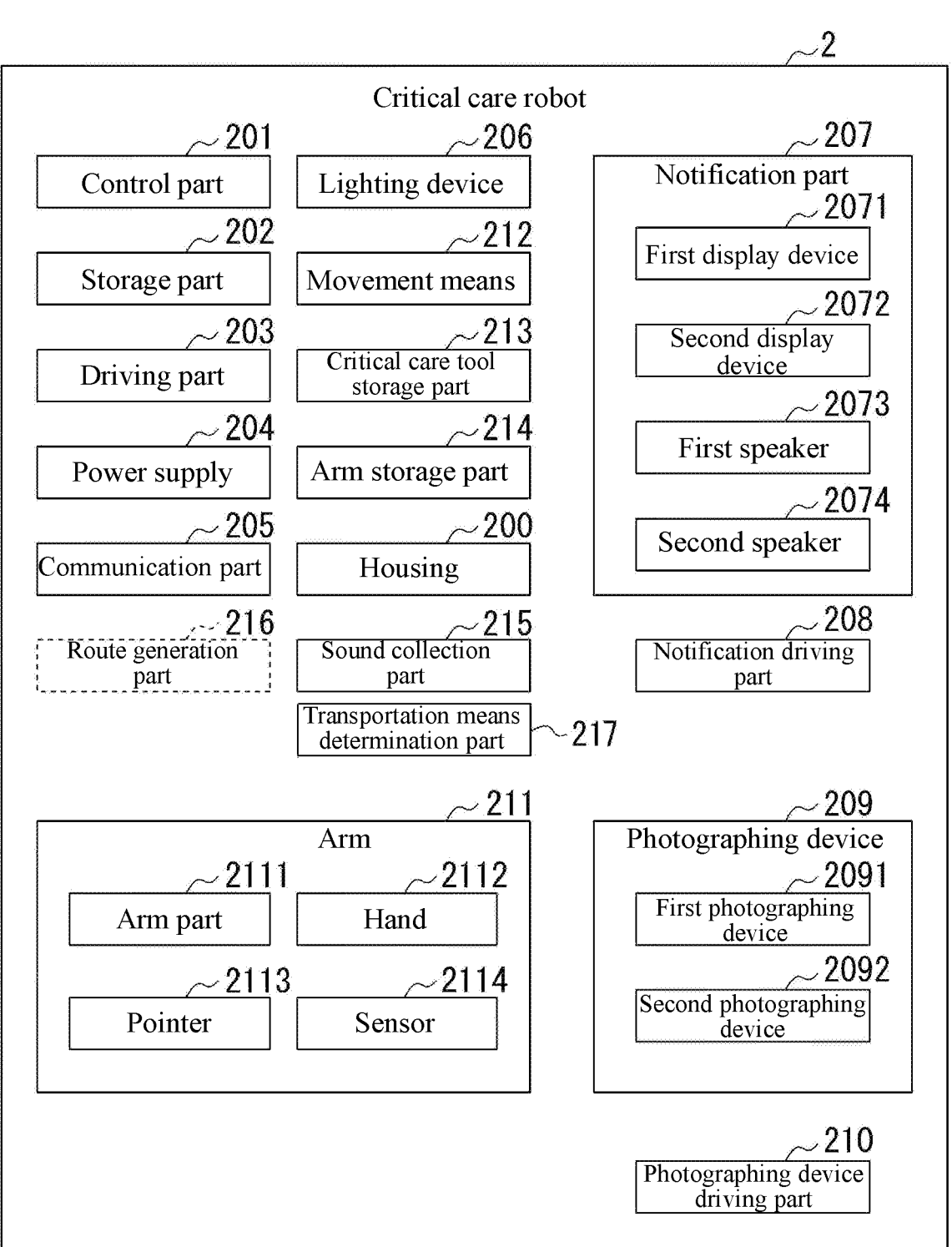
FIG. 6 is a diagram showing a configuration example of a critical care robot according to an embodiment.

FIG. 6 is a diagram showing a configuration example of a critical care robot according to an embodiment. As shown in FIG. 6, the critical care robot 2 includes, for example, a housing 200, a control part 201, a storage part 202, a driving part 203, a power supply 204, a communication part 205, a lighting device 206, a notification part 207, a notification driving part 208, a photographing device 209, a photographing device driving part 210, the arms 211, a movement means 212, a critical care tool storage part 213, an arm storage part 214, and a sound collection part 215. The configuration shown in FIG. 6 is an example, and the disclosure is not limited thereto. The critical care robot 2 may be provided with other functional parts. For example, the critical care robot 2 may include, for example, a route generation part 216. The critical care robot 2 may be provided with one or more arms 211 that can instruct with the pointer 2113 or the like.

The control part 201 controls the operation of the critical care robot 2 in response to the remote control instruction received by the communication part 205. Alternatively, the control part 201 controls the operation of the critical care robot 2 based on the program stored in the storage part 202. The control part 201 transmits an image (for example, surrounding information D2) taken by the photographing device 209 to the server 3, the doctor 101, the ambulance crew 111, and the coordinator 131 via the communication part 205. Further, the control part 201 transmits medical information such as vital checks acquired by the reporter or the person on the site by operating the critical care tool to the server 3, the doctor 101, the ambulance crew 111, and the coordinator 131 via the communication part 205. The control part 201 takes out the arms 211 from the arm storage part 214 and controls them based on, for example, remote control information. The control part 201 stores the arms 211 in the arm storage part 214 based on, for example, remote control information. The control part 201 controls the opening and closing of the critical care tool storage part 213 based on, for example, remote control information. The control part 201 controls the movement means 212 based on, for example, remote control information. The control part 201 switches between an on state and an off state of the lighting of the lighting device 206 based on the remote control information and the image taken by the photographing device 209. The control part 201 controls the operation of the arms 211 by driving the driving part 203 based on, for example, remote control information. The control part 201 outputs the information included in the remote control information to the notification part 207. The remote control information may include text information, image information, voice information, and the like. The control part 201 controls the operation of the arms 211 of the critical care robot 2 in response to the remote control instruction received from the server 3 by the communication part 205. A plurality of arms 211 may be remotely controlled by different operators (for example, a critical care technician and an assistant critical care technician). The control part 201 acquires the usage status (whether it is in use or unused) of other critical care robots around the device via the network NW, and updates the usage status information stored in the storage part 202.

The storage part 202 stores a program, a predetermined value, and the like used for control of the control part 201. The storage part 202 temporarily stores the acquired information. Further, the storage part 202 stores the position information (latitude/longitude, commercial facility name, and the like) in which the critical care robot 2 is installed and the map information around the critical care robot 2. The storage part 202 stores the algorithm used for the route search. When the installation position of the critical care reporting device 7 is fixed, the storage part 202 stores the installation position information in association with the device-specific information of the critical care reporting device 7.

The storage part 202 stores the position information in which other critical care robots around the own device are installed. The configuration of the other critical care robots may be the same as or different from that of the critical care robot 2. When the configurations are different, the storage part 202 may store the position information in association with the function of the critical care robot. The storage part 202 stores usage status information of other critical care robots around the own device.

The driving part 203 includes, for example, an actuator, a gear, and the like. The driving part 203 controls the operation of the arms 211 by the control of the control part 201.

The power supply 204 supplies electric power to each part of the critical care robot 2. The power supply 204 may include a rechargeable secondary battery, a replaceable battery, a solar cell, and the like.

The communication part 205 transmits and receives information via the network NW. The communication part 205 includes, for example, a communication circuit that can be connected to a communication line and a communication circuit that can be connected to the Internet. The communication part 205 may include a global positioning system (GPS) receiver.

The lighting device 206 switches between an on state and an off state of lighting according to the control of the control part 21. The number of lighting devices 206 may be plural.

The notification part 207 includes, for example, a first display device 2071, a second display device 2072, a first speaker 2073, and a second speaker 2074. The number of display devices and speakers included in the notification part 207 is not limited to two. The first display device 2071 or the second display device 2072 may include a touch panel sensor on the screen.

The first display device 2071 notifies the reporter on the site or people around the reporter of the information included in the remote control information.

The second display device 2072 presents, for example, the information input by the operator 122, for example, to calm the bystander or to give an instruction to the bystander. The operator 122 operates the touch panel (not shown) or the keyboard (not shown) to input the information presented to the bystander.

The first speaker 2073 notifies the reporter on the site or people around the reporter of the information included in the remote control information. The notification part 207 may convert the text information included in the remote control information into an audio signal by a conventional method and output it from the first speaker 2073.

The second speaker 2074 outputs, for example, the information input by the operator 122, for example, to calm the bystander or to give an instruction to the bystander. The operator 122 inputs the information presented to the bystander by using a microphone (not shown) or operating a keyboard (not shown).

The notification driving part 208 controls, according to the control of the control part 201, the opening and closing of the first display device 2071, the taking-out and storage of the second display device 2072 from the housing 200, and the direction and angle thereof; and the taking-out and storage of the first speaker 2073 from the housing 200 and the direction and angle thereof, and the taking-out and storage of the second speaker 2074 from the housing 200 and the direction and angle thereof. The notification part 207 of the embodiment can control the height, the vertical direction and angle, and the horizontal direction and angle, that is, the directivity can be controlled. In the embodiment, the notification driving part 208 controls the directivity of the notification part 207 in response to a remote control instruction of at least one of the critical care technician 121, the operator 122, and the assistant critical care technician 123, whereby information can be provided to the provided person or the person to convey.

The notification driving part 208 does not control the directivity by controlling the direction and angle of the speakers, but may control the directivity according to the control of the control part 201 by, for example, using two speakers and controlling the phase and the like of the audio signals output from the two speakers. The directivity control is used, for example, to ensure the safety of the site and to calm the people around the patient who are excited. Alternatively, the directivity control is used to instruct a same sex person as the patient to put on or take off his/her clothes, to instruct the surrounding people to turn their backs to the patient when performing putting on or taking off clothes, and the like.

The photographing device 209 includes a first photographing device 2091 and a second photographing device 2092. The number of photographing devices is not limited to two.

The first photographing device 2091 photographs, for example, based on a photographing instruction by a remote control of the critical care technician 121. The image to be taken is, for example, an image of the patient, an image of the surroundings where the patient is present, and the like.

The second photographing device 2092 photographs, for example, based on a photographing instruction by a remote control of the doctor 101. The image to be taken is, for example, an image of the patient, an image of an affected part of the patient, and the like.

The photographing device driving part 210 controls, according to the control of the control part 201, the taking-out and storage of the first photographing device 2091 from the housing 200 and the direction and angle thereof, and the taking-out and storage of the second photographing device 2092 from the housing 200 and the direction and angle thereof.

The arm 211 includes, for example, an arm part 2111, a hand 2112 (end effector), a pointer 2113, and a sensor 2114. As shown in FIG. 1, the critical care robot 2 includes, for example, two arms 211 (211*a*, 211*b*). Further, the arms 211 can be stored in the arm storage part 214. The arms 211 are controlled by remote control. The arms 211 can operate the critical care tool stored in the critical care tool storage part 213. The arm 211 includes an actuator (motor, artificial muscle, and the like) (not shown) driven by the driving part 203.

The arm part 2111 corresponds to a human arm, and a sensor 2114 is attached to a joint.

The hand 2112 (gripping part) corresponds to a human hand, and includes, for example, two or more fingers, and a sensor 2114 is attached to a knuckle or the like.

The pointer 2113 is, for example, a laser pointer. The pointer 2113 may be attached to, for example, the hand 2112, or may be grippable by the hand 2112. The pointer 2113 is switched between an on state and an off state by the control of the control part 201.

The sensor 2114 is an encoder that detects the movement of a joint, a tactile sensor attached to a finger or the hand 2112, or the like. The sensor 2114 outputs the detected detection value to the control part 201.

The movement means 212 is, for example, a plurality of wheels. The movement means 212 may be driven by the driving part 203. The critical care robot 2 may be moved by a person by hand carry, and at this time, the movement means 212 may be driven by the driving part 203 to assist the movement.

The critical care tool storage part 213 stores the critical care tool in, for example, a box or a bag. The critical care tool storage part 213 is not limited to one, and may be provided in two or more, for example, on the front and back sides. Each of the critical care tools has a wired or wireless communication function, and transmits the acquired data to the critical care robot 2.

The arms 211 are stored in the arm storage part 214. The arm storage part 214 is provided for each arm 211 as shown in FIG. 1.

The sound collection part 215 is a microphone or a microphone array including a plurality of microphones. The sound collection part 215 may collect an acoustic signal based on a remote control by the critical care technician 121 or the like, and may transmit the collected acoustic signal to the server 3 as environmental data (environmental information).

The route generation part 216 performs the same processing as the route generation part 306 of the server 3, for example.

Further, the route generation part 216 acquires the position information of the critical care reporting device 7, and selects the critical care robot 2 based on the acquired position information of the critical care reporting device 7. The route generation part 216 generates route information of the movement route from the selected critical care robot 2 to the critical care reporting device 7 from the self-position to the position where the critical care report is issued based on the difference between the position information where the critical care report is issued and the self-position of the critical care robot 2. Subsequently, the route generation part 216 generates navigation information from the critical care robot 2 to the critical care reporting device 7 by images and audio signals based on the generated route information. The route is not limited to the shortest distance, and may be generated in consideration of the surrounding road conditions, the number of people, the road width, and the like.

A transportation means determination part 217 performs the same processing as, for example, a transportation means determination part 307 of the server 3.

The support determination part 218 determines whether support of another critical care robot installed around the own device is necessary based on the acquired medical condition information and environmental data. The support determination part 218 determines that the support of another critical care robot is necessary, for example, when there are many people around the patient and the surrounding people cannot handle the response with their own device, or when there are multiple patients, or the like. When the support determination part 218 determines that the support of another critical care robot is necessary, the support determination part 218 transmits a support request to the server 3 via the network NW. The support request transmitted to the server 3 is added with the identification information of the own device, the installation position or identification information of another critical care robot, and the like. If it is possible to communicate with another critical care robot without going through the server 3, the critical care robot 2 may transmit a support request to the another critical care robot. The support request transmitted to another critical care robot includes position information of the patient, route information to the position of the patient, navigation information from the installation position of the another critical care robot to the position of the patient, and the like.

[Configuration Example of Server]

Next, a configuration example of the server 3 will be described.

Figure 7:
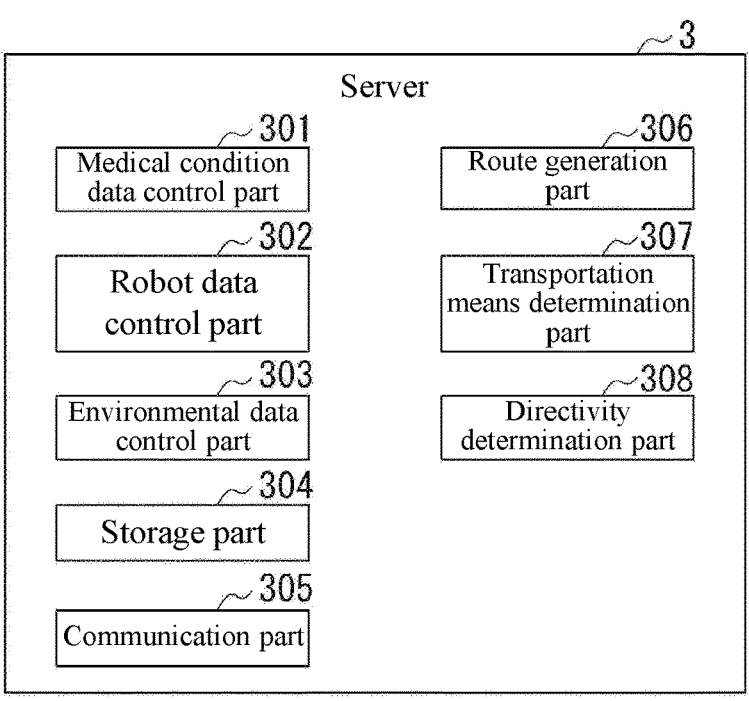
FIG. 7 is a diagram showing a configuration example of a server according to an embodiment.

FIG. 7 is a diagram showing a configuration example of a server according to an embodiment. As shown in FIG. 7, the server 3 includes, for example, a medical condition data control part 301, a robot data control part 302, an environmental data control part 303, a storage part 304, a communication part 305 (position information acquisition part), a route generation part 306, a transportation means determination part 307, and a directivity determination part 308. The configuration shown in FIG. 7 is an example, and the disclosure is not limited thereto. For example, when the critical care robot 2 includes the route generation part 216, the server 3 does not have to include the route generation part 306.

The medical condition data control part 301 acquires medical information such as vital checks from the critical care robot 2 via the communication part 305. In the following description, "medical information such as vital checks" may be referred to as "medical condition information." The medical condition information may include, for example, vital signs such as respiratory status, pulse rate, blood pressure, body temperature, consciousness level, and degree of bleeding, and the like. The medical condition data control part 301 transmits the acquired medical information such as vital checks to the terminal 6 (6-1, 6-2, 6-3, 6-4, 6-5) via the network NW.

The robot data control part 302 acquires a remote control instruction of the critical care technician 121 or the doctor 101 performing remote control via the communication part 305. The robot data control part 302 generates control command information for controlling the operation of the critical care robot 2 based on the acquired remote control instruction, and transmits the generated control command information to the critical care robot 2 via the communication part 305. The robot data control part 302 generates directivity control information that controls the direction in which the notification part 207 of the critical care robot 2 is directed based on the directivity information, and transmits the generated directivity control information to the critical care robot 2 via the communication part 305. The robot data control part 302 transmits the audio signal received from the terminal 6 to the critical care robot 2 via the communication part 305 and the network NW. The remote control instruction may also include an instruction to output an audio signal from the second speaker 2074. When the robot data control part 302 receives the support request information from the critical care robot 2, the robot data control part 302 transmits the support movement request to another critical care robot included in the support request information via the network NW. The support movement request includes position information of the patient, route information to the position of the patient, navigation information from the installation position of the another critical care robot to the position of the patient, and the like. The robot data control part 302 transmits, for example, a remote control request for another critical care robot to a terminal of another critical care technician associated with the another critical care robot.

The environmental data control part 303 acquires the environmental data photographed by the photographing device 209 from the critical care robot 2 via the communication part 305. The environmental data also includes, for example, the number of people around, ground and topography related information, and the traffic volume. The environmental data control part 303 transmits the acquired environmental data to the terminal 6 (6-1, 6-2, 6-3, 6-4, 6-5) via the network NW.

The storage part 304 stores programs, threshold values, network information, and the like used by each part of the server 3. The storage part 304 stores the position information (latitude/longitude, commercial facility name, and the like) in which the critical care robot 2 is installed and the map information around the critical care robot 2. When the installation position of the critical care reporting device 7 is fixed, the storage part 304 stores the installation position information in association with the device-specific information of the critical care reporting device 7.

The communication part 305 transmits and receives data to and from the critical care robot 2 via the network NW. The communication part 305 refers to the database 4 via the network NW. The communication part 305 transmits and receives information to and from the terminal 6 (6-1, 6-2, 6-3, 6-4, 6-5) via the network NW.

The route generation part 306 selects the critical care robot 2 installed closest to the reporter based on the position information of the reporter, or the position information of the mobile phone 5-2 or the critical care reporting device 7. The position information is generated, for example, based on the data received from the GPS satellite by the GPS receiver 51. Further, when the installation position of the critical care reporting device 7 is fixed, the route generation part 306 acquires the position information of the critical care reporting device 7 by referring to the identification information included in the critical care report and the information stored in the storage part 304. The route generation part 306 generates route information between the reporter and the critical care robot 2 by using the position information of the selected critical care robot 2 and the difference between the reporter's position information and the environmental data. The route is not limited to the shortest distance, and may be generated in consideration of the surrounding road conditions, the number of people, the road width, and the like. The route generation part 306 transmits the generated route information to the reporter's mobile phone 5-2 via the network NW. In another situation, the route generation part 306 transmits the generated route information to the critical care robot 2 via the network NW. The route generation part may be provided in the critical care robot 2.

The transportation means determination part 307 determines whether the treatment has been completed based on the acquired medical information such as vital checks and instructions from the critical care technician. When the treatment is completed and transportation may be performed by a taxi, for example, the transportation means determination part 307 transmits a dispatch stop request indicating that the dispatch of the ambulance is stopped to the terminal 6-2 of the ambulance crew 111. When it is determined that the treatment is not completed, the transportation means determination part 307 indicates that remote control is still required and transmits information to the terminal 6-3 or the like of the critical care technician 121. The critical care robot 2 may include a transportation means determination part that performs the same processing as the transportation means determination part 307.

The directivity determination part 308 determines the muzzle (directivity) toward which the notification part 207 of the critical care robot 2 is directed in response to remote control or instructions from the critical care technician 121, the operator 122 to calm the bystander, the assistant critical care technician 123, the coordinator 131, or the like. The directivity determination part 308 outputs the determined directivity information to the robot data control part 302.

In another situation, the directivity determination part 308 determines the direction (directivity) toward which the notification part 207 is directed in order to notify the route information based on the result recognized by the critical care robot 2 when the critical care robot 2 is carried to the reporter. The directivity determination part 308 may perform voice recognition processing on the acoustic signal transmitted by the critical care robot 2 and perform the image recognition processing on the image to recognize the person who carries it when the critical care robot 2 is carried to the reporter. The directivity determination part 308 determines the direction (directivity) toward which the notification part 207 of the critical care robot 2 is directed in response to remote control or instructions from the critical care technician 121, the operator 122 to calm the bystander, the assistant critical care technician 123, the coordinator 131, or the like. The directivity determination part 308 outputs the determined directivity information to the robot data control part 302.

The critical care robot 2 or the server 3 may generate traffic control information (signals, instructions to surrounding vehicles (particularly effective to automatic driving)) of the transportation route in addition to the notification of whether the ambulance crew 111 can be dispatched. The critical care robot 2 or the server 3 may transmit the generated traffic control information to, for example, a traffic control center or a critical care center. Thereby, according to the embodiment, it is possible to control the traffic of the transportation route according to the reaction method.

[Configuration Example of Terminal 6]

Next, a configuration example of the terminal 6 will be described.

Figure 8:
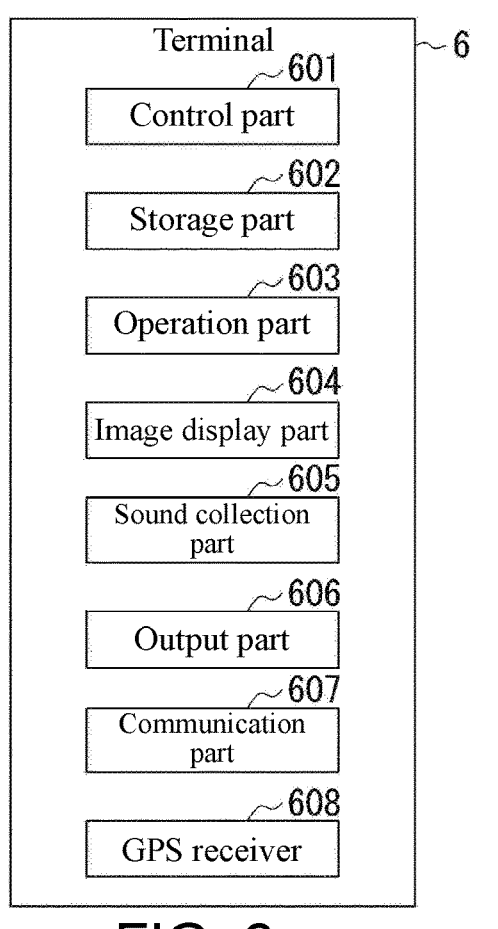
FIG. 8 is a diagram showing a configuration example of a terminal according to an embodiment.

FIG. 8 is a diagram showing a configuration example of a terminal according to the embodiment. As shown in FIG. 8, the terminal 6 includes, for example, a control part 601, a storage part 602, an operation part 603, an image display part 604, a sound collection part 605, an output part 606, and a communication part 607. The configuration of the terminal 6 shown in FIG. 8 is an example, and the disclosure is not limited thereto. The terminal 6 may include a GPS receiver 608. Further, the mobile phone 5-2 of the reporter may have the same configuration as the terminal 6 provided with the GPS receiver 608.

The control part 601 causes the image display part 604 to display the information (medical condition information, environmental data, and the like) received by the communication part 607. When the environmental data received by the communication part 607 includes an acoustic signal, the control part 601 causes the output part 606 to reproduce the acoustic signal. The control part 601 transmits the audio signal collected by the sound collection part 605 to the server 3 via the communication part 607. The control part 601 generates a remote control instruction based on the operation result detected by the operation part 603, and transmits the generated remote control instruction to the server 3 via the communication part 607. The transmitted audio signal may be associated with a remote control instruction. For example, when the operator calls from the second speaker 2074 to a person around the patient, the remote control instruction includes an instruction to output an audio signal from the second speaker 2074.

The storage part 602 stores a program, a threshold value, and the like used for control by the control part 601. The storage part 602 stores environmental data and medical condition information under the control of the control part 601.

The operation part 603 detects the operation result of the operator. The operation part 603 is, for example, a touch panel sensor provided on the image display part 604. Alternatively, the operation part 603 may be a keyboard or a mouse. Alternatively, the operation part 603 may be a joystick. Alternatively, the operation part 603 may be a glove or the like provided with a tactile sensor that detects the movement of the operator's hand.

The image display part 604 displays an image output by the control part 601.

The sound collection part 605 includes at least one microphone and collects the voice of the operator. The sound collection part 605 may be a microphone array composed of a plurality of microphones.

The output part 606 is, for example, a speaker. The output part 606 outputs an acoustic signal output by the control part 601.

The communication part 607 receives information (medical condition information, environmental data, and the like) from the server 3 via the network NW, and outputs the received information to the control part 601. The communication part 607 transmits the operation request output by the control part 601 to the server 3 via the network NW.

The GPS receiver 608 acquires the position information of the terminal 6 based on the information received from the GPS satellite. When the terminal 6 is, for example, a mobile phone or the like, the terminal 6 may acquire the position information based on the base station information.

[Configuration Example of Critical Care Reporting Device 7]

Next, a configuration example of the critical care reporting device 7 will be described.

Figure 9:
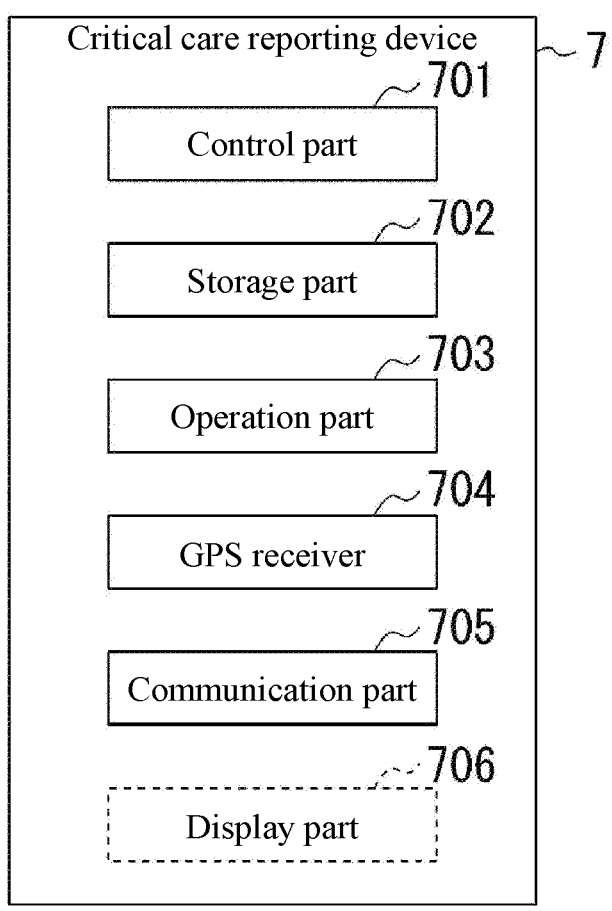
FIG. 9 is a diagram showing a configuration example of a critical care reporting device according to an embodiment.

FIG. 9 is a diagram showing a configuration example of a critical care reporting device according to the embodiment. As shown in FIG. 9, the critical care reporting device 7 includes, for example, a control part 701, a storage part 702, an operation part 703, a GPS receiver 704, and a communication part 705. The critical care reporting device 7 may include a display part 706. The configuration of the critical care reporting device 7 shown in FIG. 8 is an example, and the disclosure is not limited thereto.

When the operation part 703 is operated, the control part 701 controls the display part 706 so as to, for example, turns on the lamp or change a color or the lamp or the like. The control part 701 transmits when the operation part 703 is operated and a critical care report to the server 3 via the communication part 705 and the network NW. The critical care report includes the position information of the critical care reporting device 7. When the installation position of the critical care reporting device 7 is fixed, the control part 701 may transmit the identification information of the critical care reporting device 7 instead of the position information.

The storage part 702 stores a program, a threshold value, and the like used by the control part 701. The storage part 702 stores the identification information of the critical care reporting device 7.

The operation part 703 detects the operation of the user (reporter). The operation part 703 is, for example, a mechanical switch, a touch panel sensor, or the like.

The GPS receiver 704 uses the information received from the GPS satellites to acquire the position information of the critical care reporting device 7. When the installation position of the critical care reporting device 7 is fixed, the critical care reporting device 7 does not have to be equipped with the GPS receiver 704.

When the operation part 703 is operated, the communication part 705 transmits a critical care report to the server 3 via the network NW.

The display part 706 is, for example, at least one of a lamp, a liquid crystal display device, an organic electroluminescence (EL), and the like. The display part 706 turns on the lamp or changes the color of the lamp under the control of the control part 701, for example, when the operation part 703 is operated.

[Operation Example of Two Arms]

Next, an operation example of the two arms will be described.

Figures 10, 11:
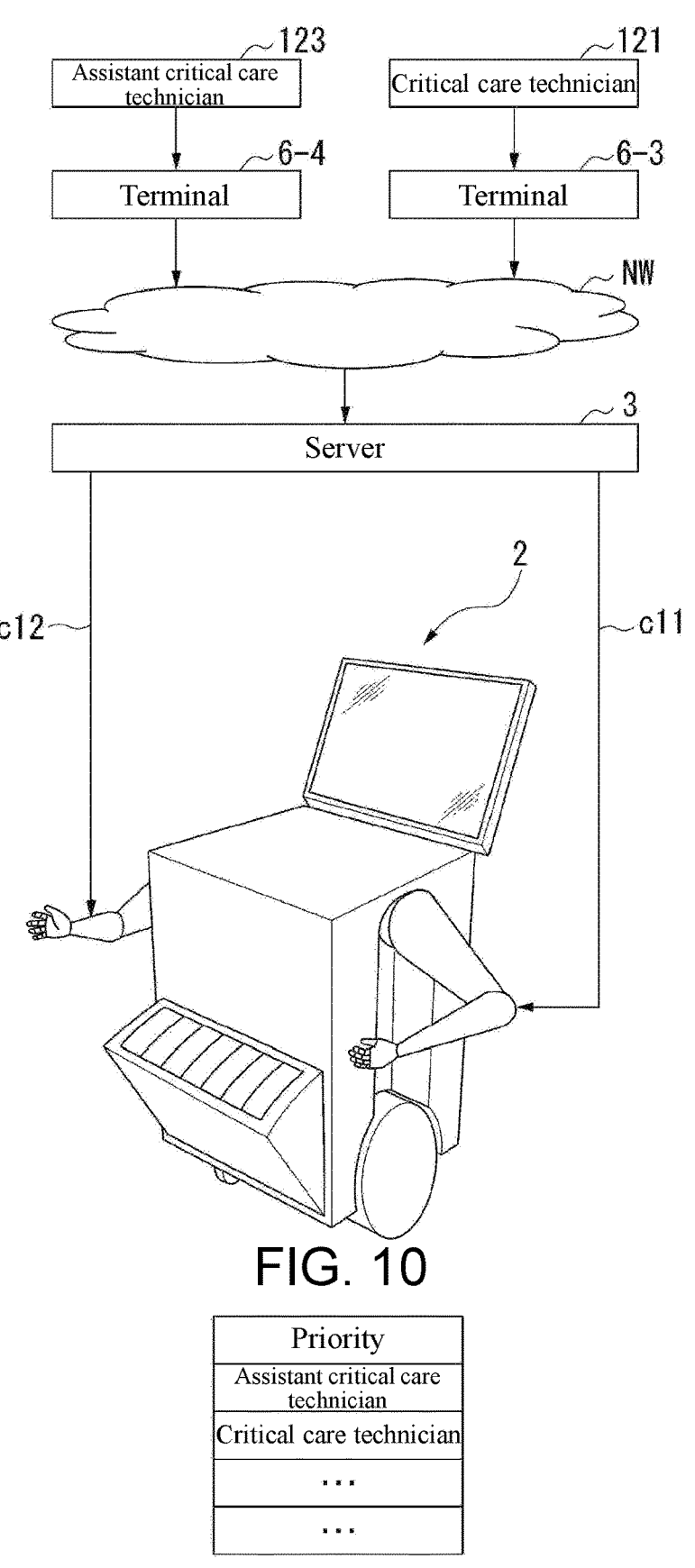
FIG. 10 is a diagram showing an operation example of two arms according to an embodiment.
FIG. 11 is a diagram showing an example of priority of arm operation according to an embodiment.

FIG. 10 is a diagram showing an operation example of two arms according to this embodiment. In the example of FIG. 10, the critical care technician 121 operates the arm 211b corresponding to the left arm by operating the terminal

6-3, and the assistant critical care technician 123 operates the arm 211a corresponding to the right arm by operating the terminal 6-4. The server 3 receives operation requests from the terminals 6-3 and 6-4, extracts which of the received operation request is the operation request for each of the arms 211, and generates remote control information for each of the arms 211. The operation request includes, for example, identification information of the terminal 6, information indicating the arm 211 to be operated, and the like. Further, the storage part 304 of the server 3 stores the identification information of the terminal 6 in association with the user. The server 3 transmits the generated remote control information to the critical care robot 2 via the network NW, so that the two arms of the critical care robot 2 can be remotely controlled by another operator.

In the example shown in FIG. 10, although an example in which the left and right arms 211 are remotely controlled by different remote operators has been described, the two arms 211 may be remotely controlled by one remote operator (for example, the critical care technician 121).

Further, when both arms 211 are remotely controlled by, for example, the critical care technician 121, a veteran assistant critical care technician 123 may want to operate the arms 211. In such a case, two remote operators cannot operate the same arms 211 at the same time.

Therefore, in the embodiment, priority is set for the operation of the arms 211. FIG. 11 is a diagram showing an example of priority of arm operation according to this embodiment. In the example of FIG. 8, the priority of the assistant critical care technician 123 is set higher than the priority of the critical care technician 121. The information regarding such priority may be stored in advance in the storage part 304 of the server 3, and may be set by a critical care technician or the like for each critical care.

Based on such priority, the server 3 generates remote control information. For example, when the critical care technician 121 is remotely controlling the arms 211 and the server 3 receives an operation request for the arms 211 from the terminal 6-4 used by the high-priority assistant critical care technician 123, the server 3 controls the arms 211 by changing the operation right of the arms 211 from the critical care technician 121 to the assistant critical care technician 123 based on the priority. That is, the robot data control part 302 of the server 3 transfers the control right of the operator having a low priority to the operator having a high priority. In this case, the server 3 may transmit information indicating that the priority has been changed to the terminals 6-3 and 6-4. In the above-mentioned example, the operation right of the arms 211 for both arms has been changed from the critical care technician 121 to the assistant critical care technician 123, but the disclosure is not limited thereto. For example, when the critical care technician 121 is operating both arms 211 and the assistant critical care technician 123 requests the operation of the arm 211a corresponding to the right arm, the server 3 switches the operation of the arm 211a from the instruction of the critical care technician 121 to the instruction of the assistant critical care technician 123.

As a result, according to the embodiment, one critical care robot can be remotely controlled smoothly and efficiently by a plurality of operators, so that rescue can be performed efficiently.

In the above-mentioned example, the example of two remote operators has been described, but the number of remote operators may be three or more. Further, the number of arms 211 may be three or more.

[Example of Notification Using Directivity Notification Part]

Next, an example of notification using the directivity notification part 207 will be described.

Figure 12:
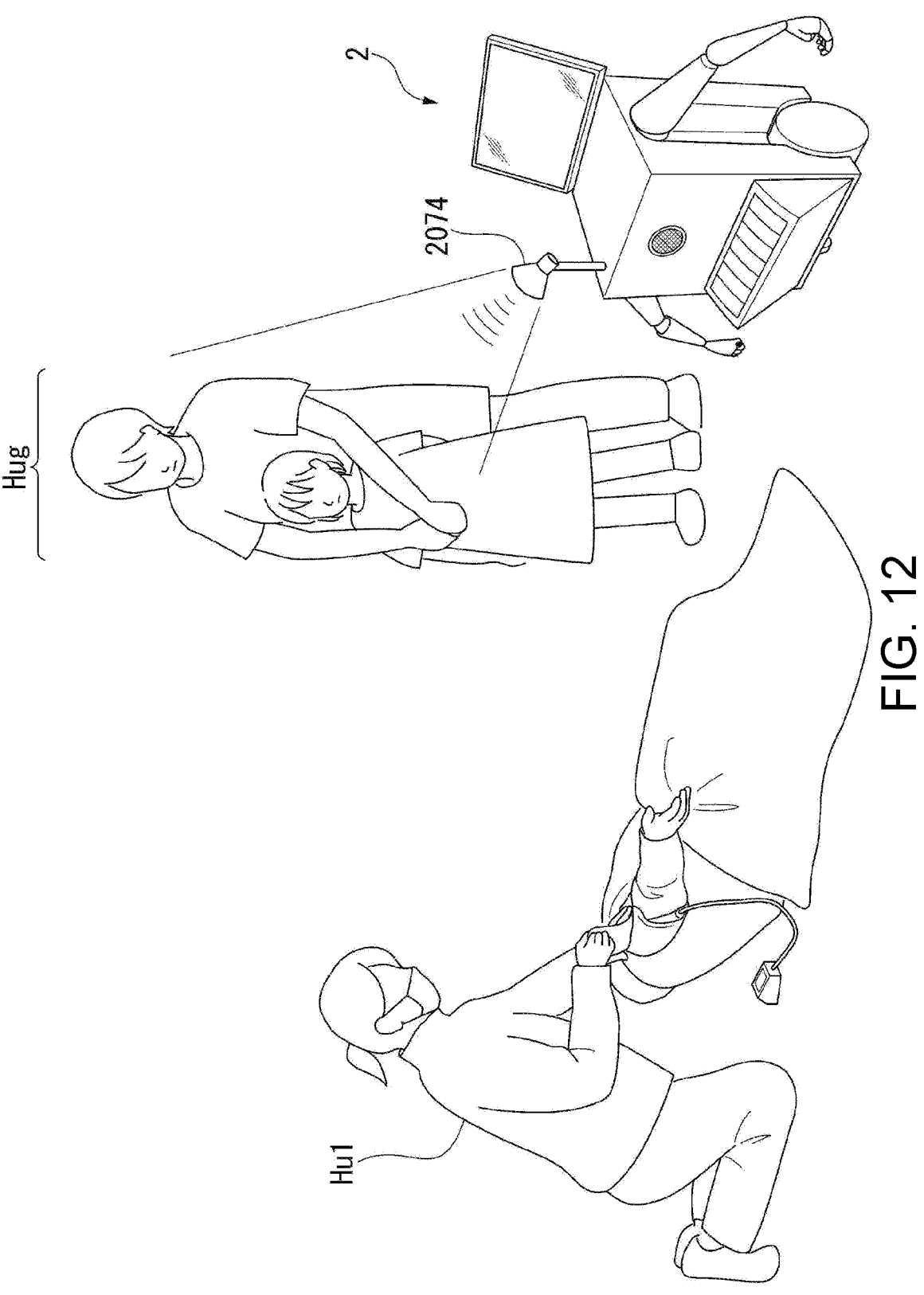
FIG. 12 is a diagram showing an example of notification using a directivity notification part according to an embodiment.

FIG. 12 is a diagram showing an example of notification using a directivity notification part according to this embodiment. In the example of FIG. 12, for example, the reporter Hu1 is treating the patient. If the place where the treatment is performed is, for example, a shopping center where there are many people, there may be many people in the vicinity in addition to the patient and the person performing the treatment. In such cases, some of the people in the vicinity may panic.

Therefore, in the embodiment, the remote operator operates the terminal 6 to direct the notification part (for example, the second speaker 2074) at the people Hug to whom warning and the like is to be conveyed, and the audio signal picked up by the terminal 6 is notified to the people Hug to whom warning and the like is to be conveyed. The critical care robot 2 or the server 3 estimates the direction of the people Hug to whom warning and the like is to be conveyed by a conventional sound source method estimation processing or the like for the acoustic signal picked up by the sound collection part 215 of the critical care robot 2. The critical care robot 2 or the server 3 may estimate the direction of the people Hug to whom warning and the like is to be conveyed by using the result of performing a conventional image processing on the image taken by the photographing device 209.

[Example of Processing of Acquired Information]

Next, an example of processing information acquired by the critical care robot 2 will be described.

The server 3 transmits medical information such as vital checks acquired by the critical care robot 2 to each terminal 6 in real time, for example. The medical information such as vital checks may be stored in each terminal 6 or the like.

Figure 13:
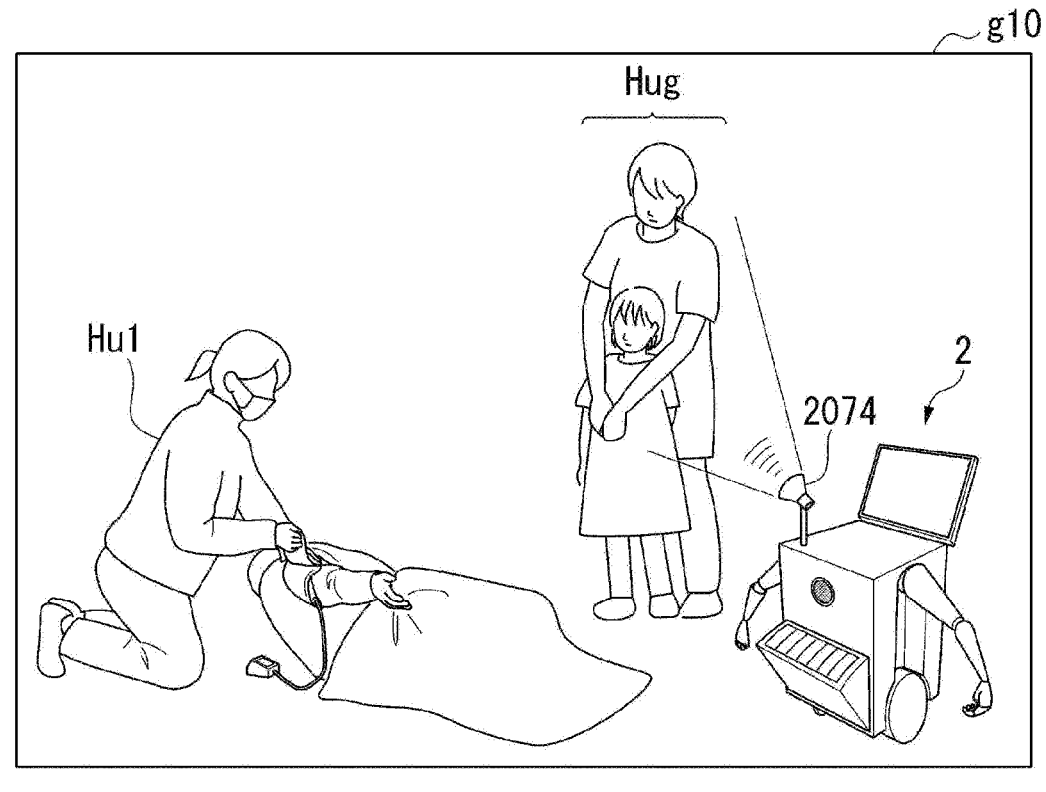
FIG. 13 is a diagram showing an example of an acquired image and an example of a stored image according to an embodiment.
Figure 13:
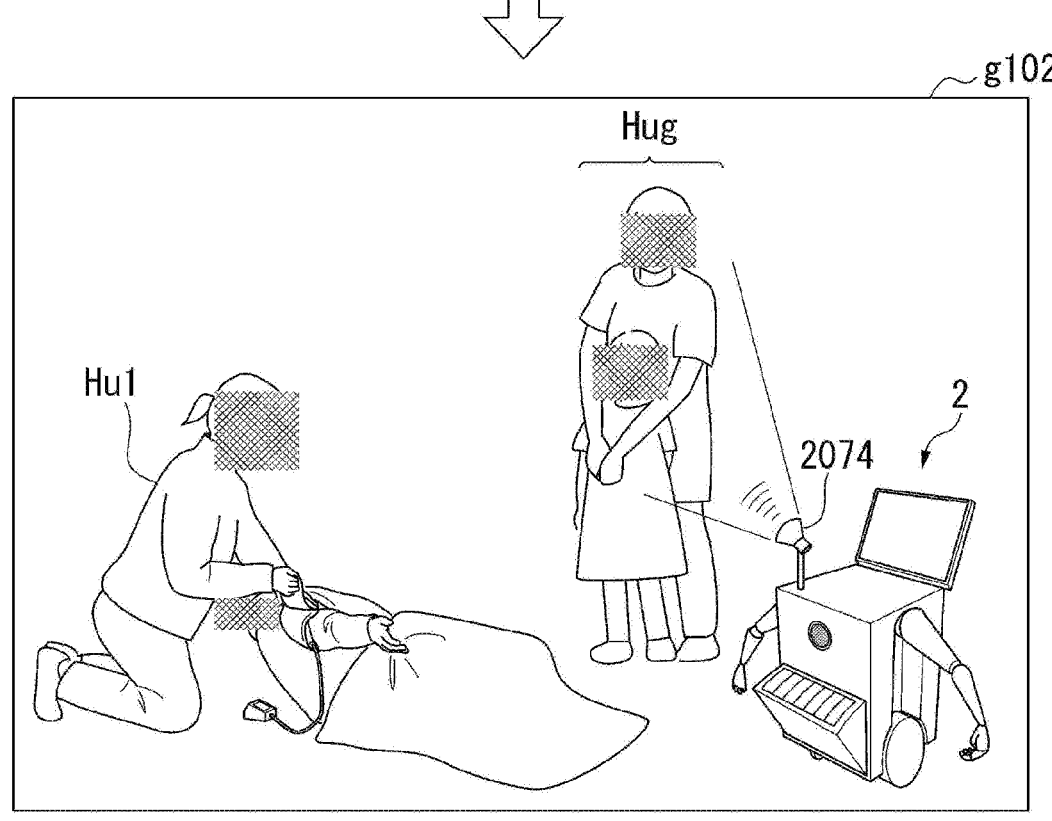

FIG. 13 is a diagram showing an example of an acquired image and an example of a stored image according to this embodiment.

The server 3 transmits the image (environmental data) taken by the photographing device 209 to each terminal 6. This image information may be stored in each terminal 6 or the like, but the image g101 acquired for privacy protection may be mosaicked (image g102) at the time of storage or the image may be blurred. The server 3 gives such a processing instruction for privacy protection to the image (environmental data), and transmits the image (environmental data) to which the processing instruction is given to each terminal 6. The processing performed at the time of storage is not limited to the mosaic processing and the blurring processing, and may be other image processing.

[Operation Example of Photographing Device]

Next, an operation example of the photographing device will be described.

Figure 14:
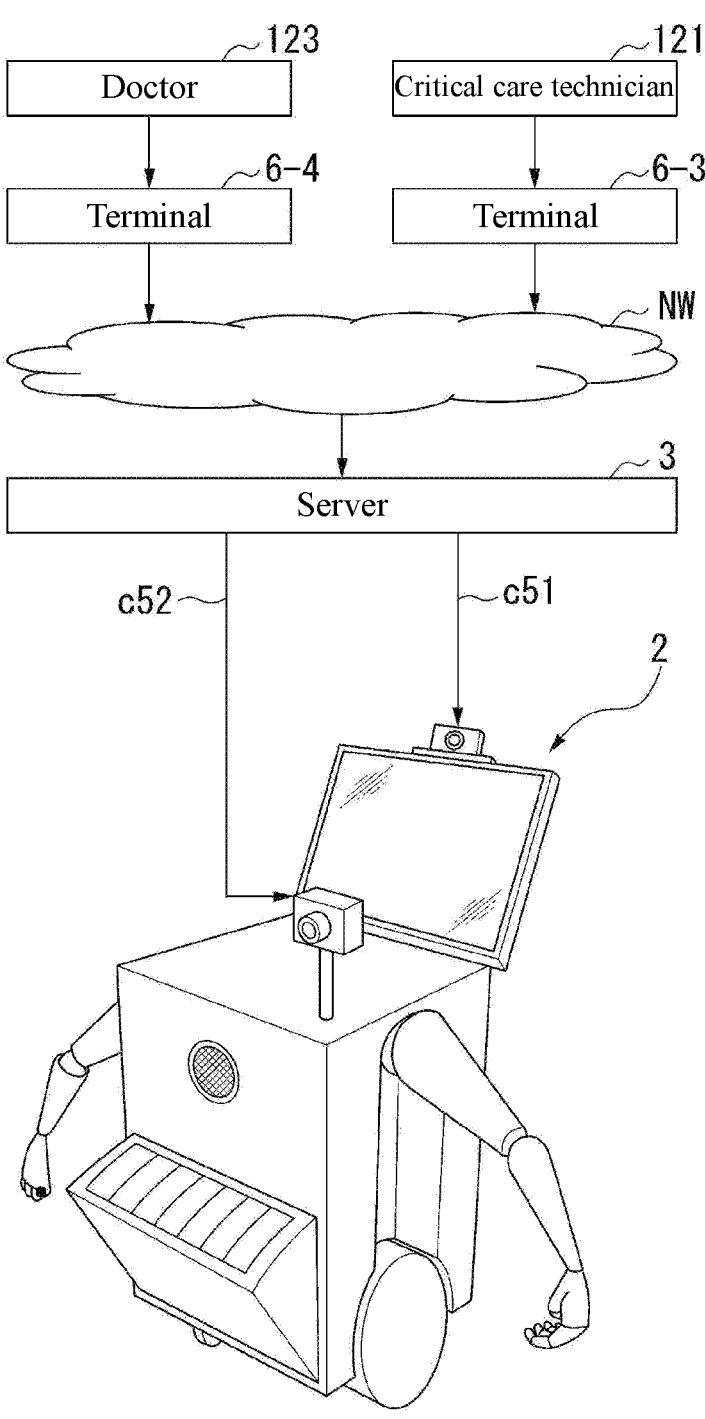
FIG. 14 is a diagram showing an operation example of two photographing devices according to an embodiment.

FIG. 14 is a diagram showing an operation example of two photographing devices according to this embodiment. In the example of FIG. 14, the critical care technician 121 operates the first photographing device 2091 by operating the terminal 6-3, and the assistant doctor 101 operates the second photographing device 2092 by operating the terminal 6-4. The operation instruction to the photographing device 209 includes the angle of view of photography, the center position of photography, and the like.

Figure 15:
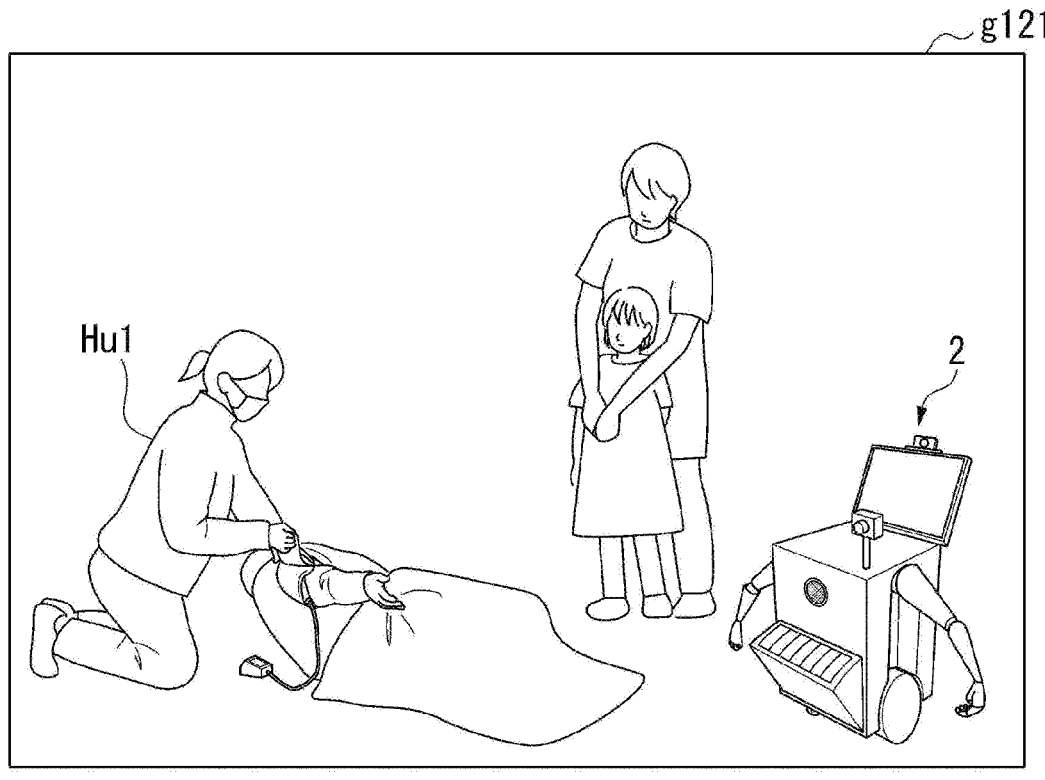
FIG. 15 is a diagram showing an example of an image taken by two photographing devices according to an embodiment.
Figure 15:
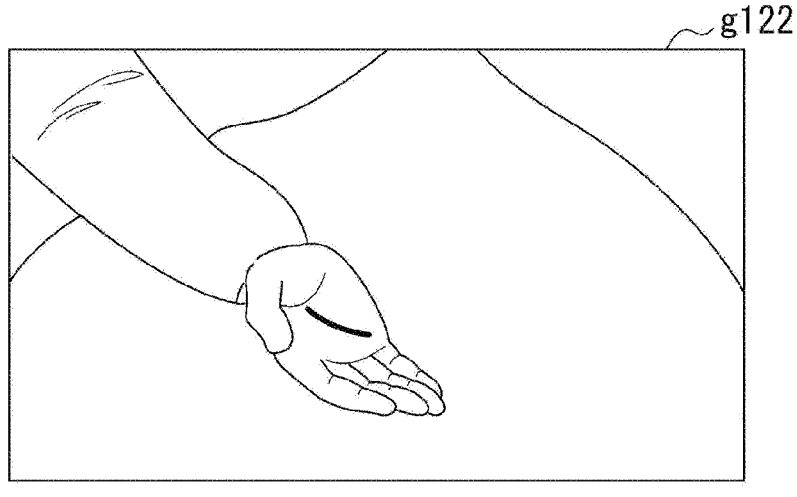

FIG. 15 is a diagram showing an example of an image taken by two photographing devices according to this embodiment. The critical care technician 121 operates the terminal 6-4 to take an image g121 necessary for treatment or acquisition of medical condition information or instruction by, for example, the first photographing device 2091.

The doctor 101 may want to confirm the patient's condition or the image of the affected part at a different angle or a different angle of view from the image g121. In such a case, the doctor 101 operates the terminal 6-1 to take a necessary image g122 by, for example, the second photographing device 2092.

[Determination of Transportation Method and Determination of Destination Hospital]

Next, a method of determining the transportation method of the patient and a method of determining a destination hospital will be described.

Figure 16:
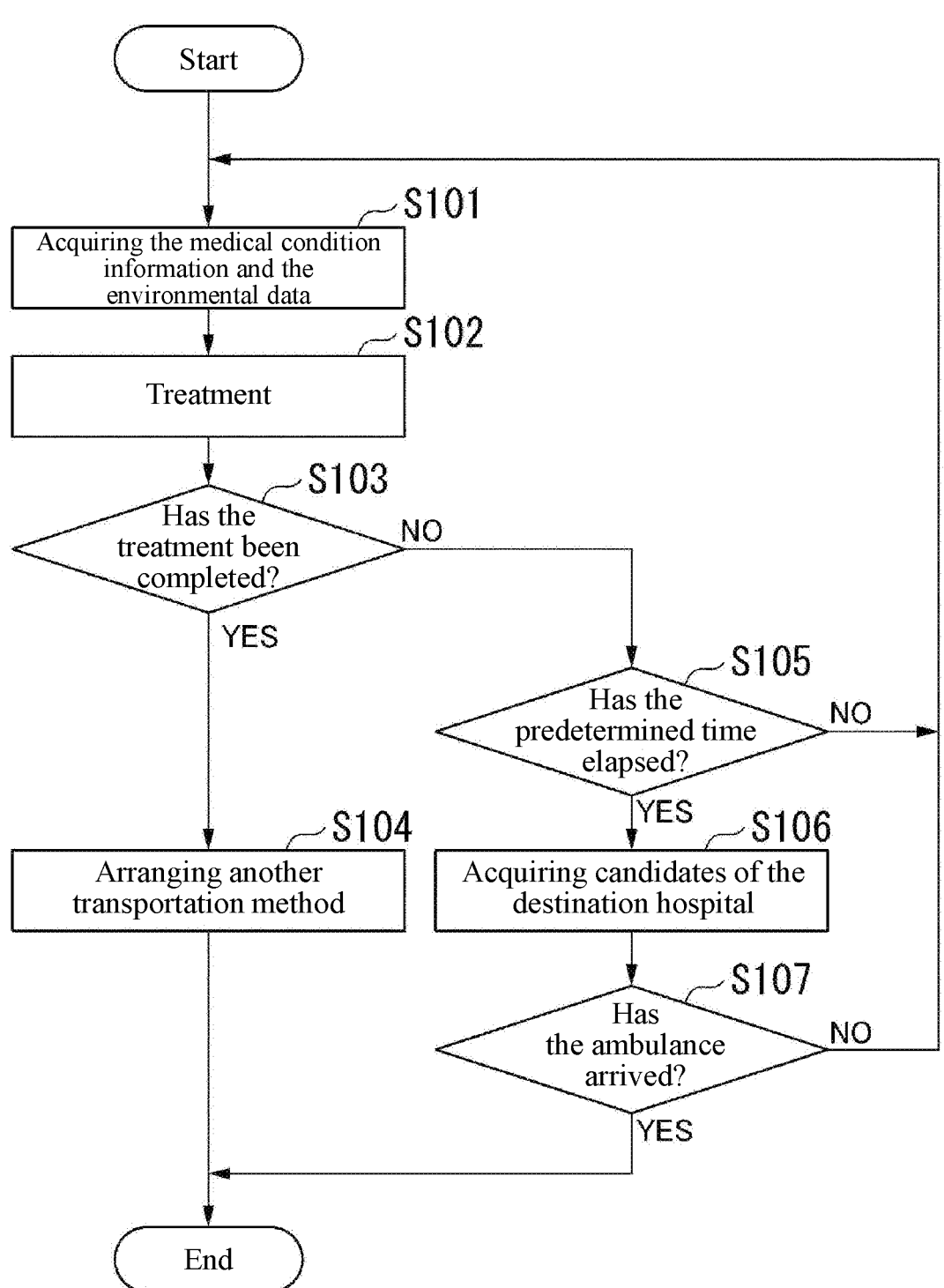
FIG. 16 is a flowchart of a procedure for determining a patient transportation method and a procedure for determining a destination hospital according to an embodiment.

FIG. 16 is a flowchart of a procedure for determining a patient transportation method and a procedure for determining a destination hospital according to this embodiment.

(Step S101) The server 3 acquires medical condition information and environmental data from the critical care robot 2 via the network NW. Subsequently, the server 3 transmits the acquired medical condition information and the environmental data to each terminal 6 via the network NW.

(Step S102) For example, the critical care technician 121 remotely controls the critical care robot 2 by operating the terminal 6-4 based on the medical condition information and the environmental data received by the terminal 6-4 to give an instruction of treatment or the like or to give a treatment. The server 3 controls the critical care robot 2 based on the remote control instruction received from the terminal 6-4 to give a treatment or an instruction on the patient.

(Step S103) For example, the critical care technician 121 determines whether the treatment for the patient has been completed based on the acquired medical condition information and environmental data. In addition, for example, the server 3 may determine whether the treatment for the patient is completed based on the medical condition information and the environmental data. The critical care technician 121 operates the terminal 6-4 to input a determination result as to whether the treatment for the patient is completed, and the terminal 6-4 transmits the determination result to the server 3 via the network 3. The server 3 determines whether the treatment for the patient has been completed based on the determination result received from the terminal 6-4. When the server 3 determines that the treatment for the patient has been completed (YES in step S103), it proceeds to the processing in step S104. When the server 3 determines that the treatment for the patient has not been completed (NO in step S103), it proceeds to the processing of step S105.

(Step S104) The server 3 transmits information indicating that the treatment has been completed to each terminal 6 via the network NW. The coordinator 131 determines that transportation by ambulance is unnecessary based on the medical condition information, environmental data, and information indicating that the treatment has been completed acquired by the terminal 6-5. The coordinator 131, the assistant critical care technician 123, or the like may determine that the patient is to be transported by another transportation means. The coordinator 131 operates the terminal 6-5 and inputs the determination result that it is determined that the transportation by the ambulance is unnecessary. The terminal 6-5 transmits the determination result to the server 3 via the network NW. The coordinator 131 arranges for other transportation means (for example, by taxi). The coordinator 131 may be responsible for notifying the ambulance to stop dispatching and arranging other transportation means, or the server 3 receiving this information may be responsible for the arrangement. When the coordinator 131 determines that the patient is to be transported to the hospital by another transportation means, the coordinator 131 may determine the hospital (for example, the family surgery) based on the medical condition information and the environmental data. The terminal 6-5 may transmit the medical condition information and the personal information to the determined hospital based on the result of the operation by the coordinator 131. The server 3 may receive this information and transmit the medical condition information and personal information to the determined hospital.

(Step S105) The server 3 determines whether a predetermined time has elapsed since the treatment was started by remote control, for example. The predetermined time is the time within the time when the ambulance is expected to arrive after the critical care report is sent. When the server 3 determines that the predetermined time has elapsed (YES in step S105), it proceeds to the processing of step S106. When the server 3 determines that the predetermined time has not elapsed (NO in step S105), it returns to the processing of step S101.

(Step S106) Since the treatment has not been completed even after the lapse of a predetermined time, the server 3 determines that it is better to transport the patient to the hospital. Subsequently, as a result of determining that it is better to transport the patient to the hospital, the server 3 transmits an instruction requesting selection of the transportation destination to the terminal 6-5 used by the coordinator 131 via the network NW. The server 3 adds the patient's personal information (medical history and the like) to the instruction requesting the selection of the transportation destination and transmits the instruction. The coordinator 131 inputs the information of the candidates of the destination hospital by operating the terminal 6-5 based on the information received by the terminal 6-5 (medical condition information, environmental data, and instruction requesting the selection of the destination). The terminal 6-5 transmits the information of the candidates of the destination hospital to the server 3 via the network NW. The server 3 acquires the information of the candidates of the destination hospital transmitted by the terminal 6-5 via the network NW.

(Step S107) The server 3 determines whether an ambulance has arrived, for example, based on the operation result of the terminal 6-2 by the ambulance crew 111. When the server 3 determines that the ambulance has arrived (YES in step S107), the server 3 ends the procedure for determining the patient transportation method and the determination processing for the destination hospital. When the server 3 determines that the ambulance has not arrived (NO in step S107), it returns to the processing of step S101.

[Example of Navigation by Critical Care Robot 2]

Next, an example of navigation by the critical care robot 2 will be described.

Figure 17:
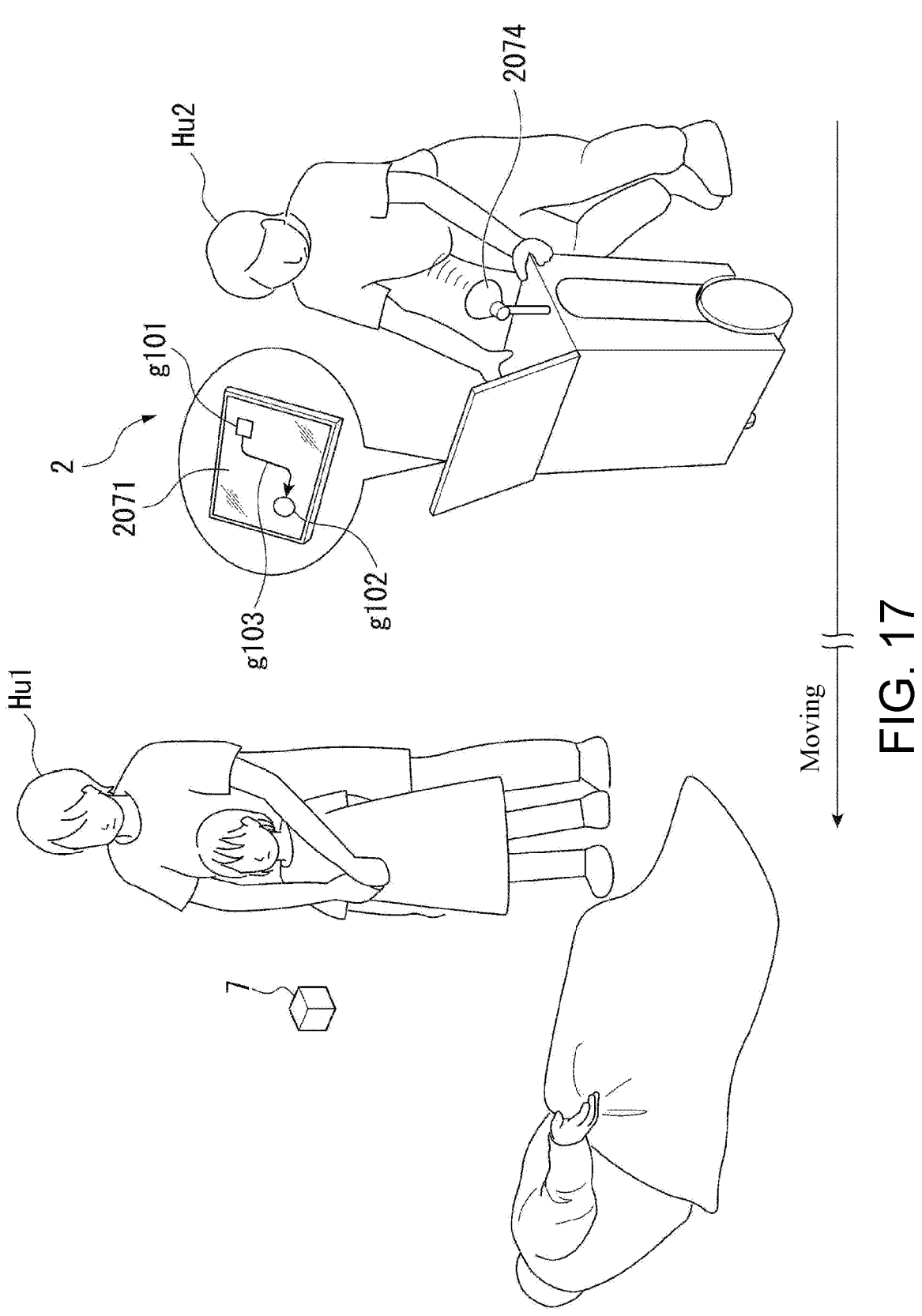
FIG. 17 is a diagram showing an example of navigation by a critical care robot according to an embodiment.

FIG. 17 is a diagram showing an example of navigation by a critical care robot according to an embodiment. In the example of FIG. 17, the patient discoverer Hu1 operates the critical care reporting device 7 to make a critical care report. The critical care robot 2 displays an image of the route information received from the server 3 in response to the critical care report on, for example, the first display device 2071, outputs an audio signal from the second speaker 2074, and notifies the surrounding person Hu2. The critical care robot 2 may drive the movement means 212 to assist the movement when moving.

As shown in FIG. 17, the first display device 2071 displays the route g103 from the current position g101 where the critical care robot 2 is installed to the position g102 (that is, the position where the patient is) of the critical care reporting device 7. Such image information may be generated by the critical care robot 2 or the server 3 based on the route information. The audio signal is, for example, "Turn left at the next corner." As the route g103, a route having a width that allows a person to move the critical care robot 2 is selected.

Figure 18:
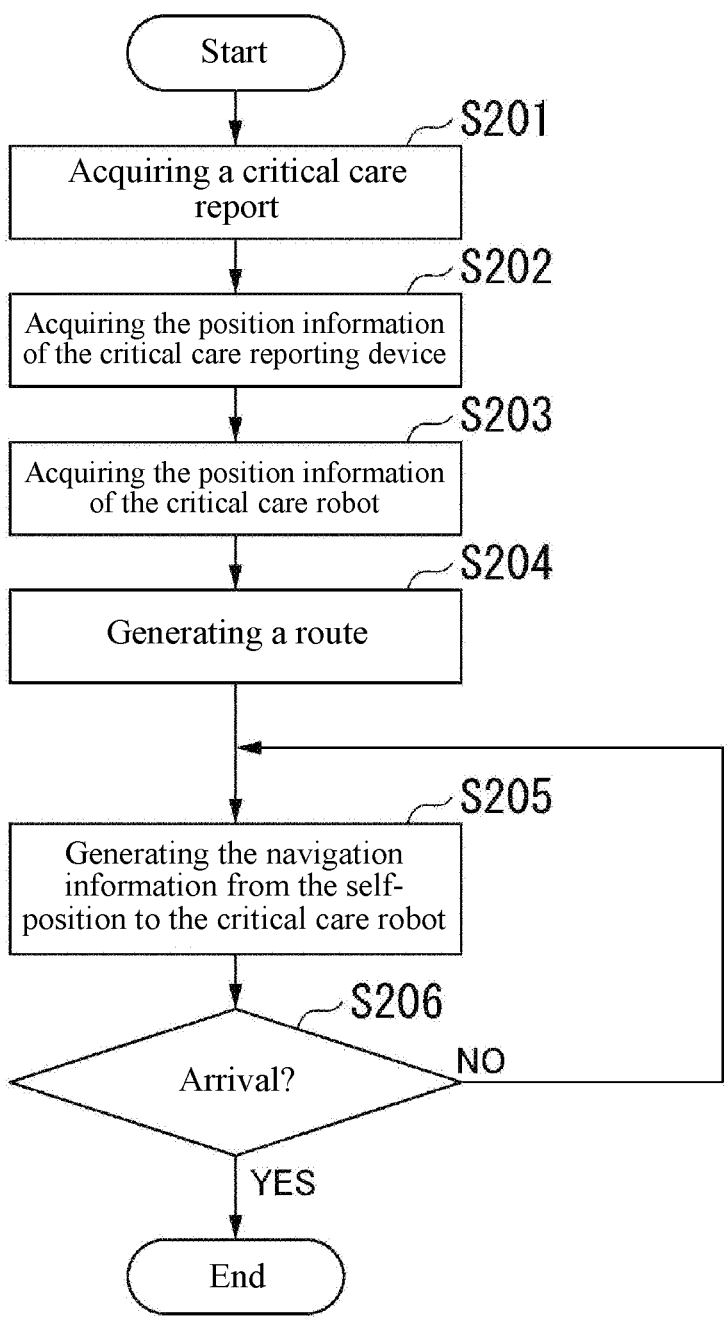
FIG. 18 is a flowchart of a procedure for generating route information of a critical care robot according to an embodiment.

FIG. 18 is a flowchart of a procedure for generating route information of a critical care robot according to an embodiment.

(Step S201) The control part 201 acquires the critical care report transmitted by the critical care reporting device 7 via the network NW.

(Step S202) The control part 201 acquires the position information of the critical care reporting device 7.

(Step S203) The route generation part 216 selects the critical care robot 2 using the position information of the critical care reporting device 7 and the information stored in the storage part 304, and acquires the position information of the selected critical care robot 2.

(Step S204) The route generation part 216 generates the route information of the critical care reporting device 7 from the critical care robot 2 by using the information stored in the storage part 202.

(Step S205) The route generation part 216 generates navigation information from the critical care robot 2 to the critical care reporting device 7 by images and audio signals based on the generated route information.

(Step S206) The control part 201 acquires, for example, the position information of the moving critical care robot 2 every second, and determines whether the critical care robot 2 has arrived at the position of the critical care reporting device 7. When the control part 201 determines that the critical care robot 2 has arrived (YES in step S206), the control part 201 ends the processing. When the control part 201 determines that the critical care robot 2 has not arrived (NO in step S206), it returns to the processing of step S205.

It should be noted that the server 3 may perform at least one processing of the generation of the route information and the generation of the navigation information shown in FIG. 18.

Further, in the above-mentioned example, the example in which the critical care robot 2 generates and navigates the route information from the installation position of the critical care robot 2 to the installation position of the critical care reporting device 7 has been described, but the disclosure is not limited thereto.

When the critical care robot 2 is reusable, it is preferable that the critical care robot 2 is returned to the place where the critical care robot 2 was installed by a person around it. In this case, the critical care robot 2 has already acquired the current position and the place where the critical care robot 2 was installed. Therefore, in the return route, the critical care robot 2 generates route information from the current position to the position where the critical care robot 2 was installed based on the difference between the current position and the position where the critical care robot 2 was installed in step S204. The critical care robot 2 may perform navigation by notifying the route information and the navigation information of the return route from the notification part 207 in the same manner as the outward route. The critical care robot 2 may generate route information and navigation information of the return route in the route information and navigation information of the outward route. The critical care robot 2 may assist the movement by a person by driving the movement means 212 in the return route as well. Further, the route information and navigation information of the outward route and the return route may be the same or different depending on the environmental data and the like. For example, on the outward route, time may be prioritized in order to perform the treatment as soon as possible, and on the return route, it may take time and the ease of movement may be prioritized.

As a result, according to the embodiment, it is possible to reduce the labor of returning the critical care robot 2 to its original position after the treatment.

[Determination of Transportation Method and Determination of Destination Hospital]

Next, a method of determining the transportation method of the patient and a method of determining a destination hospital will be described with reference to FIGS. 19 and 20.

Figure 19:
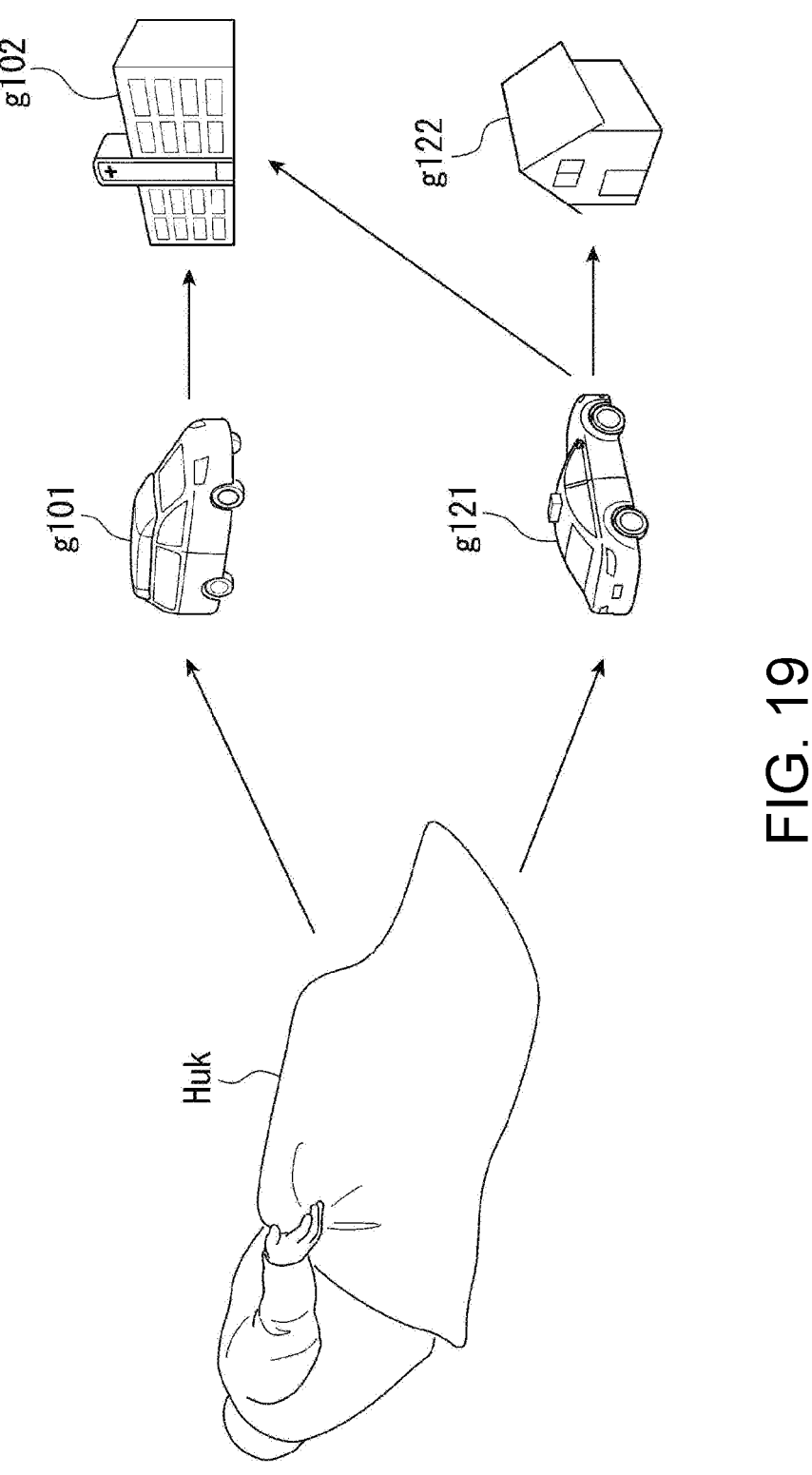
FIG. 19 is a diagram showing an example of a transportation destination.
Figure 20:
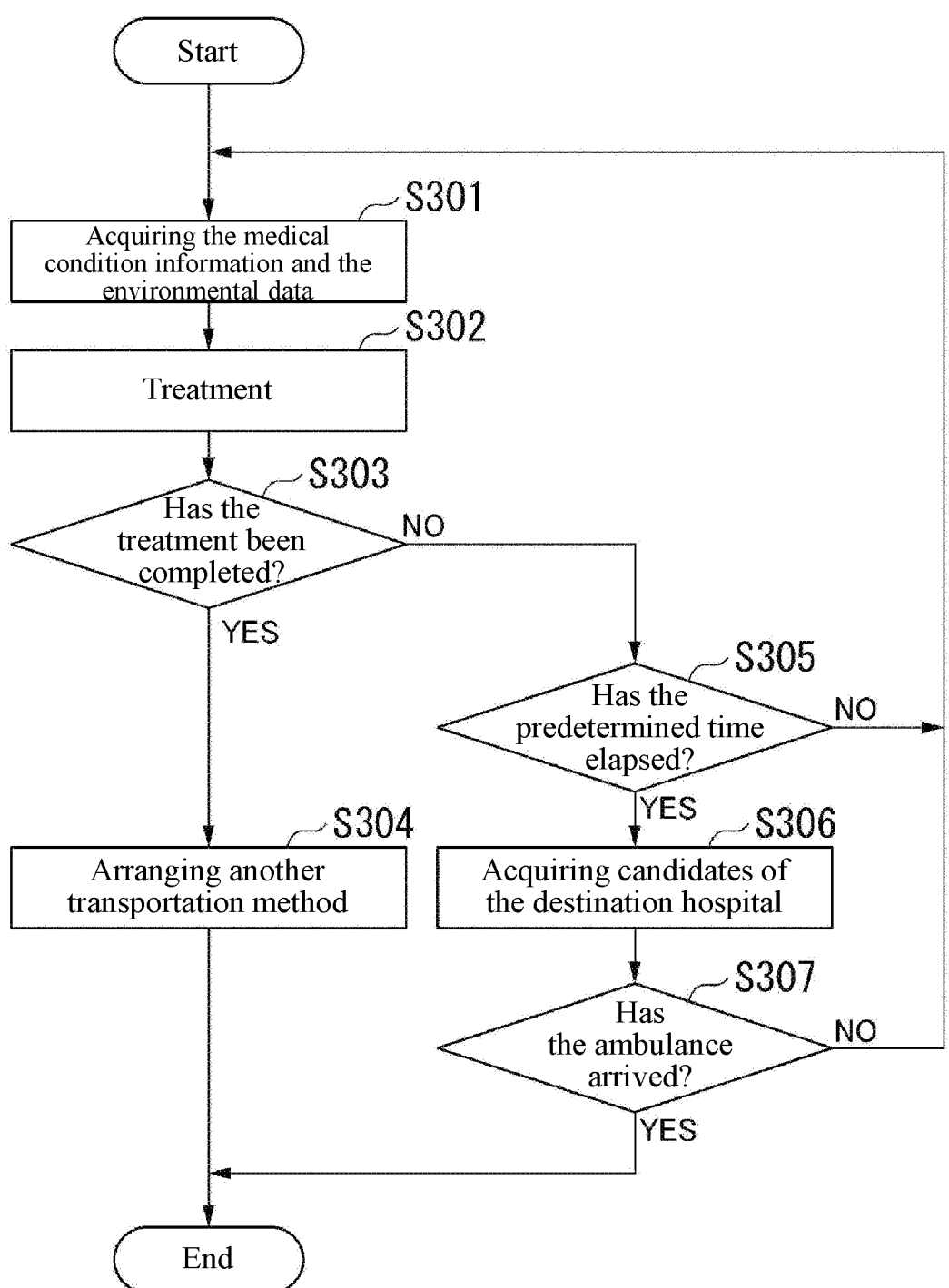
FIG. 20 is a flowchart of a procedure for determining a patient transportation method according to an embodiment.

FIG. 19 is a diagram showing an example of a transportation destination. FIG. 20 is a flowchart of a procedure for determining a patient transportation method according to an embodiment.

(Step S101) The server 3 acquires medical condition information and environmental data from the critical care robot 2 via the network NW. Subsequently, the server 3 transmits the acquired medical condition information and the environmental data to each terminal 6 via the network NW.

(Step S202) For example, the critical care technician 121 remotely controls the critical care robot 2 by operating the terminal 6-4 based on the medical condition information and the environmental data received by the terminal 6-4 to give an instruction to the reporter or the like or to make the critical care robot 2 perform treatment of the patient Huk. The server 3 controls the critical care robot 2 to perform treatment of the patient Huk and give instructions to the reporter and the like based on the remote control instruction received from the terminal 6-4.

(Step S103) For example, the critical care technician 121 determines whether the treatment for the patient Huk has been completed based on the acquired medical condition information and environmental data. The critical care technician 121 operates the terminal 6-4 to input the determination result of whether the treatment of the patient Huk has been completed. The terminal 6-4 transmits the determination result to the server 3 via the network NW. The transportation means determination part 307 determines whether the treatment of the patient Huk has been completed based on the determination result received from the terminal 6-4. The transportation means determination part 307 may determine whether the treatment of the patient Huk has been completed based on the medical condition information and the environmental data. When the transportation means determination part 307 determines that the treatment of the patient Huk has been completed (YES in step S203), it proceeds to the processing in step S104. When the transportation means determination part 307 determines that the treatment of the patient Huk has not been completed (NO in step S203), it proceeds to the processing in step S105.

(Step S204) The transportation means determination part 307 determines to transport the patient Huk by another transportation means based on the medical condition information and the environmental data acquired from the critical care robot 2. Subsequently, the transportation means determination part 307 transmits an ambulance dispatch stop instruction to the terminal 6-2 of the ambulance crew 111 via the network NW. Subsequently, the transportation means determination part 307 arranges for another transportation means (for example, a taxi g121). After the processing, the transportation means determination part 307 ends the processing. The coordinator 131, the critical care technician 121, or the like may determine that the patient is to be transported by another transportation means. In this case, the transportation means determination part 307 may give an ambulance dispatch stop instruction and arrange for another transportation means based on at least one of the determination result of the coordinator 131 or the critical care technician 121, the medical condition information, and the environmental data. Further, even when the treatment is completed, the transportation means determination part 307 may determine a hospital (for example, a family surgery) based on the medical condition information and the environmental data in the same manner as in step S206, and transmit the medical condition information and personal information to the determined hospital. Therefore, the destination where the patient Huk is transported by another transportation means g121 may be the home g122 or the like, or the hospital g102.

(Step S205) The transportation means determination part 307 determines whether a predetermined time has elapsed since the treatment was started by remote control, for example. The predetermined time is the time within the time when the ambulance g101 is expected to arrive after the critical care report is sent. When the transportation means determination part 307 determines that the predetermined time has elapsed (YES in step S206), it proceeds to the processing of step S106. When the server 3 determines that the predetermined time has not elapsed (NO in step S205), it returns to the processing of step S201.

(Step S206) The coordinator 131 lists candidates of the destination hospital as a determination result indicating that the patient should be transported to the hospital based on the medical condition information and the environmental data acquired by the terminals 6-5. The terminal 6-5 transmits the hospital candidate information of the transport destination to the server 3 via the network NW based on the operation result of the coordinator 131. The transportation means determination part 307 arranges the hospital g102 based on at least one of the medical condition information, the environmental data, and the determination result, and transmits the personal information and the medical condition information of the patient to the arranged hospital g102. As a result, according to the embodiment, the destination hospital can acquire the patient's medical condition information before the patient is transported, and thus can prepare for receiving the patient. In the embodiment, a "plurality of transportation means" is, for example, a transportation means by an ambulance, a transportation means by a taxi, a transportation means by an attendant's car when there is an attendant, and the like.

(Step S207) The server 3 determines whether an ambulance g101 has arrived, for example, based on the operation result of the terminal 6-2 by the ambulance crew 111. When the server 3 determines that the ambulance g101 has arrived (YES in step S207), it ends the processing of determining the patient transportation method. When the server 3 determines that the ambulance g101 has not arrived (NO in step S207), it returns to the processing of step S201.

The critical care robot 2 or the server 3 may generate traffic control information (signals, instructions to surrounding vehicles (particularly effective to automatic driving)) of the transportation route in addition to the notification of whether the ambulance crew 111 can be dispatched. The critical care robot 2 or the server 3 may transmit the generated traffic control information to, for example, a traffic control center or a critical care center. Thereby, according to the embodiment, it is possible to control the traffic of the transportation route according to the reaction method.

[Example of Movement Method of Another Critical Care Robot Whose Support is Requested]

Here, an example of a movement method of another critical care robot whose support is requested will be described.

The another critical care robot may be allowed to be self-propelled and moved by the server 3 or another critical care technician by remotely controlling a terminal.

Alternatively, the another critical care robot may notify the route information and the navigation information received from the server 3 or the critical care robot 2 to a person around the another critical care robot so that it may be moved to the position where the patient is.

Alternatively, route information and navigation information to the position of another critical care robot may be printed out and passed to a person around the patient by, for example, a printing device (not shown), and the another critical care robot may be brought to by the person around the patient.

The above-mentioned movement method is an example, and the disclosure is not limited thereto.

[Example of Notification Using Directivity Notification Part]

Next, an example of notification using the directivity notification part 207 will be described.

Figure 21:
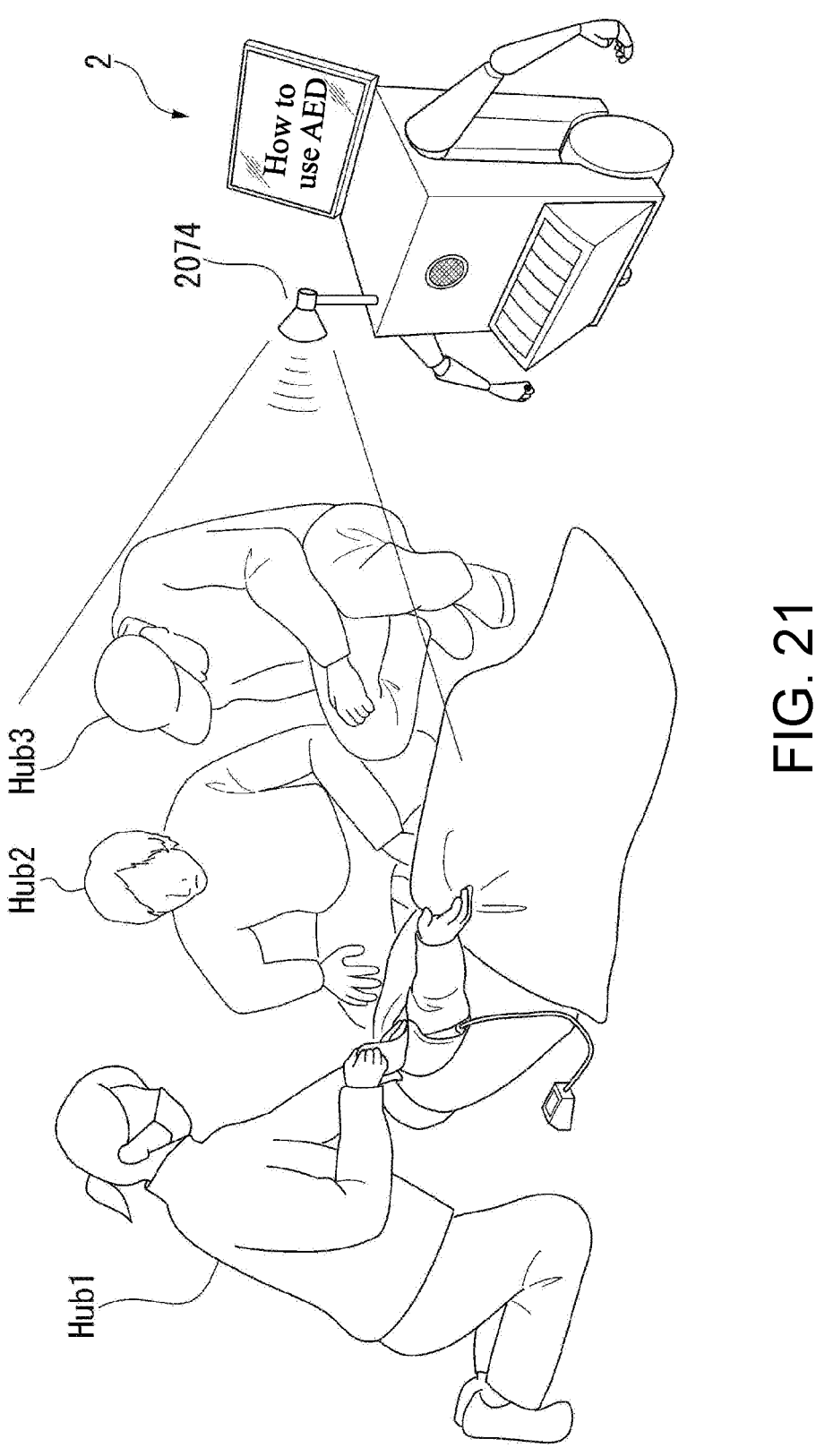
FIG. 21 is a diagram showing an example of notification using a directivity notification part according to an embodiment.

FIG. 21 is a diagram showing an example of notification using a directivity notification part according to this embodiment. In the example of FIG. 21, for example, the reporter Hub1 is treating the patient. There are bystanders (people who are present at the critical care site) Hub2 and Hub3 around the patient and the reporter Hub1. For example, if the critical care technician 121 determines that support in addition to the reporter Hub1 is necessary for the treatment of the patient, the critical care technician 121 selects a person whose support can be requested based on the environmental data acquired by the terminal 6-3. For example, when there are multiple people in the vicinity, the critical care technician 121 selects a person from, for example, people other than children and the elderly. Alternatively, if the critical care technician 121 needs to undress the patient, the critical care technician 121 selects a person of the same sex as the patient.

The critical care technician 121 inputs the selection result by operating the terminal 6-3. The terminal 6-3 transmits the input (or selected) selection result to the server 3 via the network NW. The server 3 generates a remote control instruction for notifying the selected person based on the received selection result, and transmits the generated remote control instruction to the critical care robot 2 via the network NW.

The notification driving part 208 of the critical care robot 2 controls the directivity to notify the selected people Hub2 and Hub3 in response to the received remote control instruction. The notification driving part 208 controls the directivity by controlling the direction and angle of the second display device 2072 and the second speaker 2074, for example. Alternatively, the notification driving part 208 controls the directivity by controlling the phases of the audio signals of the first speaker 2073 and the second speaker 2074. Alternatively, the notification driving part 208 controls the directivity by controlling, for example, a polarizing filter of a liquid crystal control method provided in the second display device 2072. The notification driving part 208 may estimate and track the directions of the selected people by a conventional sound source method estimation processing or the like on the acoustic signal collected by the sound collection part 215 of the critical care robot 2. Further, the notification driving part 208 may estimate and track the directions of the selected people by using the result of performing conventional image processing on the image taken by the photographing device 209. The above-mentioned directivity control method is an example, and the disclosure is not limited thereto.

The information to be notified may be information input by operating the operation part 603 of the terminal 6-3, may be an audio signal collected by the sound collection part 605, or may be information stored in advance by the critical care robot 2 or the server 3 or the like. The contents to be notified include, for example, a request for cooperation and how to use the critical care tools.

Thereby, in the embodiment, the remote operator operates the terminal 6 to control the directivity of the notification part 207 to the people to whom warning and the like is to be conveyed, and to notify the people to whom the notification content is to be conveyed.

Figure 22:
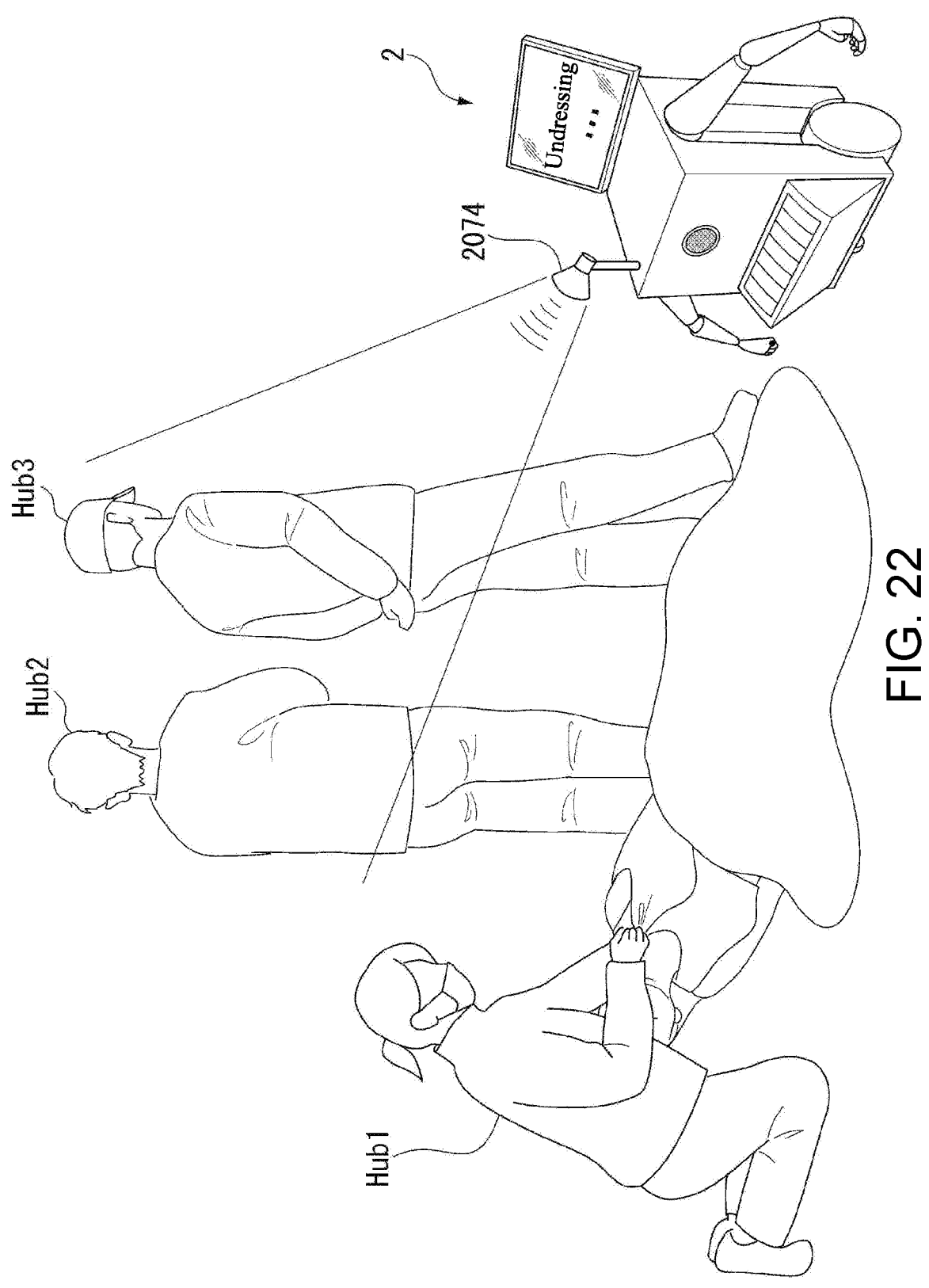
FIG. 22 is a diagram showing protection of patient privacy using a directivity notification part according to an embodiment.

FIG. 22 is a diagram showing an example of protection of patient privacy using a directivity notification part according to an embodiment. In the example of FIG. 22, the patient is a female, the surrounding person Hub1 who is treating the patient is a female, and the surrounding people Hub2 and Hub3 are males. For example, if an AED needs to be used, the person who is treating the patient will need to undress the patient's clothing. In such a case, in order to protect the privacy of the patient, it is necessary to make the treatment perform by a person with the same sex, and it is necessary to prevent the opposite sex from seeing the patient and to prevent the patient from being seen by other people in the vicinity.

In such a case, the critical care technician 121 operates the terminal 6-3 to input to form a wall by turning people's backs to the patient so that the patient being treated is not seen by people of the opposite sex and is not seen by others. The notification driving part 208 of the critical care robot 2 controls the directivity of the notification part 207 to notify the target people in response to the remote control instruction generated based on the input content.

[Directivity Control Procedure of Notification Part 207 and Method of Support Request to Another Critical Care Robot]

Next, the control procedure for controlling the directivity of the notification part 207 for the person who helps the treatment and the procedure for requesting support from another critical care robot will be described.

Figure 23:
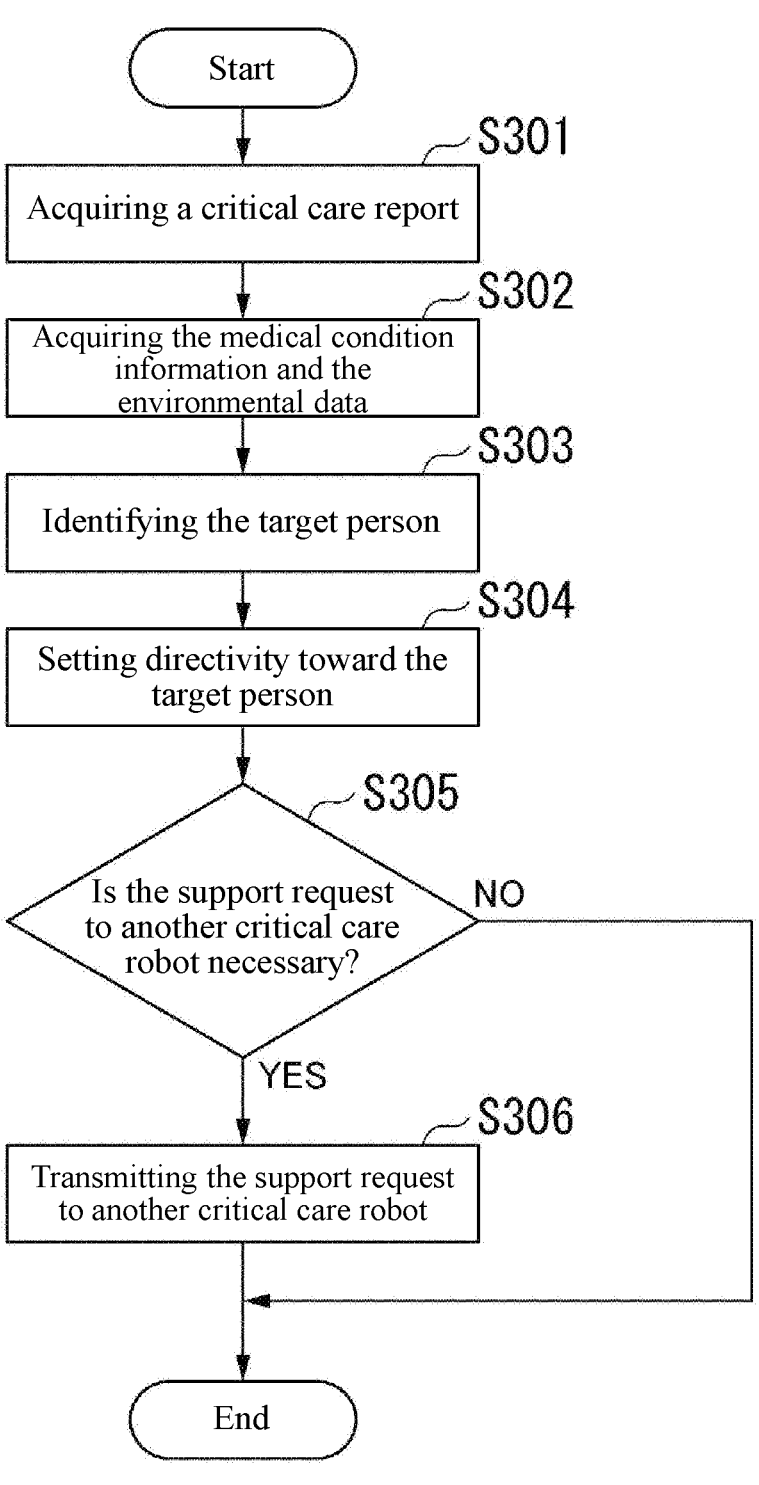
FIG. 23 is a flowchart of a directivity control procedure of a notification part and a support request procedure to another critical care robot according to an embodiment.

FIG. 23 is a flowchart of a directivity control procedure of the notification part 207 and a support request procedure to another critical care robot according to the embodiment.

(Step S301) The server 3 acquires the critical care report issued by the reporter's mobile phone 5-2. Subsequently, the server 3 transmits the acquired critical care report to each terminal 6.

(Step S302) The critical care technician 121 operates the terminal 6-3 to instruct the critical care robot 2 to make the reporter or the like perform a treatment or use a critical care tool, or to make the critical care robot 2 perform a treatment or use a critical care tool. The critical care robot 2 acquires medical condition information and environmental data, and transmits the acquired medical condition information and environmental data to the server 3 via the network NW. The server 3 transmits the acquired medical condition information and the environmental data to each terminal 6 via the network NW.

(Step S303) The critical care technician 121 selects a target person to request for his or her support for treatment or the like from the surrounding people based on the medical condition information and the environmental data. The critical care technician 121 operates the terminal 6-3 to input the selection result.

(Step S304) The server 3 sets the directivity toward the target person based on the selection result received from the terminal 6-3. The critical care robot 2 may set the directivity toward the target person. The server 3 transmits a remote control instruction including directivity control information of the notification part 207, a request content, and the like to the critical care robot 2 via the network NW. The critical care robot 2 controls the directivity of the notification part 207 to notify people to be notified according to the received remote control instruction.

(Step S305) The support determination part 218 determines whether support of another critical care robot installed around the own device is necessary based on the acquired medical condition information and environmental data. The critical care technician 121 may determine whether a support request to another critical care robot is necessary based on the medical condition information and the environmental data. In this case, the critical care technician 121 may operate the terminal 6-3 to input and transmit the determination result of the support request, so that the support determination part 218 may acquire the determination result. When the determination result of the support request is that the support request to another critical care robot is necessary (YES in step S305), the support determination part 218 proceeds to the processing of step S306. When the determination result of the support request is that the support request to another critical care robot is not necessary, the support determination part 218 ends the processing (NO in step S305).

(Step S306) When the support determination part 218 determines that the support of another critical care robot is necessary, the support determination part 218 transmits a support request to the server 3 via the network NW.

In FIG. 23, it is determined whether the support of another critical care robot is necessary after the target person is selected from the surrounding people, but the disclosure is not limited thereto. The critical care system 1 may select a target person from the surrounding people after determining whether the support of another critical care robot is necessary, or may perform two processings at the same time.

[Processing Example of Critical Care System 1]

Figure 24:
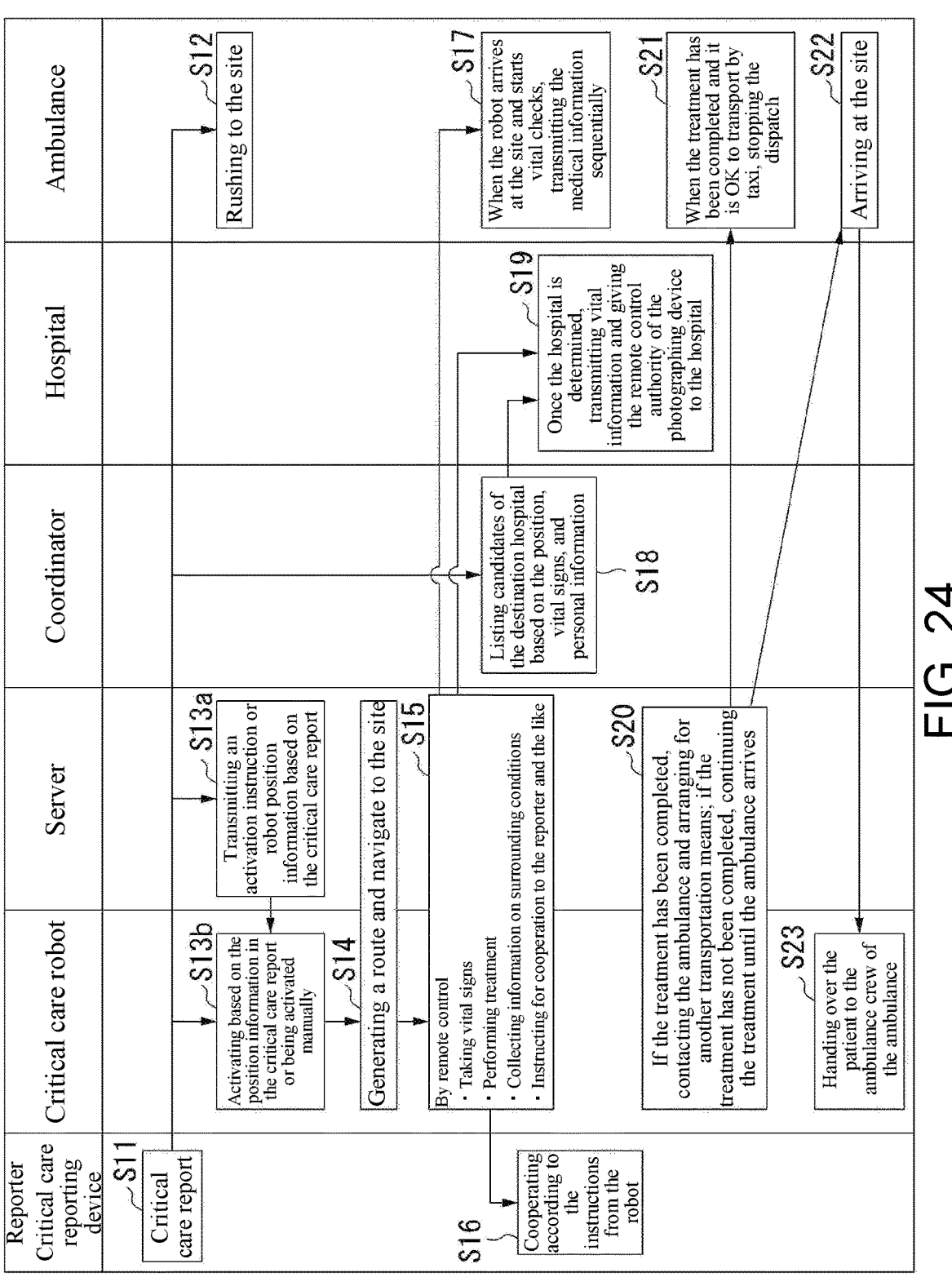
FIG. 24 is a diagram showing a processing example of a critical care system according to an embodiment.

Next, a processing example of the critical care system 1 of the embodiment will be described with reference to FIGS. 4, 6 to 9, and 24. FIG. 24 is a diagram showing a processing example of a critical care system according to an embodiment. In addition, in FIG. 24, the "critical care robot" is also referred to as the "robot." In addition, the example shown in FIG. 24 is an example in which the critical care robot 2 does not touch a person such as a patient and gives instructions to surrounding people by, for example, the light of the pointer 2113.

(Step S11) When the reporter finds a patient, the reporter makes a call to request critical care (critical care report) using the mobile phone 5-2. In addition, this critical care report is, for example, transmitted to the critical care robot 2, the server 3, the terminal 6-2 of the ambulance crew 111, the terminal 6-3 of the critical care technician 121, the terminal 6-4 of the assistant critical care technician, and the terminal 6-5 of the coordinator 131. The critical care report includes at least position information such as the address of the site. The critical care report may include information such as the patient's condition, environmental condition, number of patients, and commercial facility name. The environmental condition is, for example, information such as traffic conditions at the site, information such as the site being a shopping center, and information such as temperature and humidity at the site. It should be noted that the server 3 may acquire the position information such as the address of the site based on the position information of the reporter's mobile phone 5-2.

(Step S12) The ambulance (not shown) starts rushing to the site in response to the critical care report. After the processing, the critical care system 1 performs at least one processing of step S13a or step S13b.

(Step S13a) In response to the critical care report, the server 3 activates the critical care robot 2 installed closest to the position based on the position information included in the critical care report. Alternatively, in response to the critical care report, the server 3 transmits the position information of the critical care robot 2 installed closest to the position to the mobile phone 5-2 based on the position information included in the critical care report. Further, the server 3 transmits the request for the critical care, the identification information of the critical care robot 2 to be used, and the like to each terminal 6.

(Step S13b) The critical care robot 2 installed closest to the position is activated based on the position information included in the critical care report. Alternatively, the reporter moves to the place where the critical care robot 2 is installed and activates the critical care robot 2 based on the position information of the critical care robot 2 transmitted to the mobile phone 5-2. The critical care technician 121 may activate the critical care robot 2 in response to the critical care report. Further, the server 3 transmits the request for the critical care, the identification information of the critical care robot 2 to be used, and the like to each terminal 6.

(Step S14) The critical care robot 2 moves to the notified position based on the position information included in the critical care report. Alternatively, the reporter moves the critical care robot 2 to the position where the patient is. In response to the critical care report, the critical care technician 121 may remotely control the critical care robot 2 to move it to the notified position.

In another case, the critical care robot 2 generates route information of the movement route from the selected critical care robot 2 to the critical care reporting device 7 in response to the critical care report. Subsequently, the critical care robot 2 generates navigation information from the critical care robot 2 to the critical care reporting device 7 by images and audio signals based on the generated route information. Subsequently, the critical care robot 2 notifies the surrounding people of the received route information and navigation information, and urges support for movement to the critical care reporting device 7. Subsequently, the critical care robot 2 navigates from the critical care robot 2 until it arrives at the critical care reporting device 7 based on the route information and the navigation information.

(Step S15) The critical care technician 121 remotely controls the critical care robot 2 to give an instruction to the reporter or a person at the site by, for example, displaying on the first display device 2071, notifying from the first speaker 2073, or using the pointer 2113. The critical care technician 121 remotely controls the critical care robot 2 to explain how to use critical care tools to the reporter or a person at the site and have them acquire medical information such as patient vital checks by, for example, displaying on the first display device 2071, notifying from the first speaker 2073, or using the pointer 2113. The critical care robot 2 transmits the acquired medical information such as vital checks to the server 3 via the network NW. Further, the critical care technician 121 remotely controls the critical care robot 2 to instruct the reporter or a person at the site to perform treatment on the patient by, for example, displaying on the first display device 2071, notifying from the first speaker 2073, or using the pointer 2113. Further, the critical care technician 121 remotely controls the critical care robot 2 to acquire environmental data (image data and acoustic signal) which is information on the surrounding condition. The critical care robot 2 transmits the acquired environmental data to the server 3 via the network NW. The remote operator gives an operation instruction by the terminal, and the server 3 that has acquired the operation instruction controls the notification part 207, the hand 2112, and the pointer of the critical care robot 2 to give an instruction or notification. Further, the server 3 (medical condition data control part 301, robot data control part 302, environmental data control part 303) performs the control operation of the arms 211 of the critical care robot 2, the driving control of the notification driving part 208, and the driving control of the photographing device driving part 210 based on the acquired remote instruction.

(Step S16) The reporter (or a person around the patient) takes out the critical care tools, performs treatment, or uses the critical care tools to obtain medical information such as vital checks according to the instruction of the critical care robot 2.

(Step S17) After the critical care robot 2 arrives at the site where the patient is, medical information such as vital checks from the critical care robot 2 is transmitted to the terminal 6-2 of the ambulance crew 111 on board the ambulance via the network NW and the server 3. The medical information such as vital checks from the critical care robot 2 is also transmitted to the terminal 6-3 of the critical care technician 121 who remotely controls the critical care robot 2.

(Step S18) Medical information such as vital checks from the critical care robot 2 is transmitted from the server 3 to the terminals 6-5 of the coordinator 131. In addition, personal information of the patient (medical history, family surgery, and the like) is transmitted from the server 3 to the terminals 6-5 of the coordinator 131. The coordinator 131 lists candidates of the destination hospital based on medical information such as vital checks and personal information acquired by terminals 6-5. The coordination and determination of the destination hospital may be performed by the coordinator 131 or by the server 3.

(Step S19) After the destination hospital is determined, medical information such as vital checks from the critical care robot 2 is transmitted from the server 3 to the terminal 6-1 of the hospital 100. Subsequently, the server 3 gives the operator of the terminal 6-1 (for example, the doctor 101) the authority to use the photographing device 209 of the critical care robot 2 when the photographing device 209 is not used by remote control. As a result, the doctor 101 can check the patient's condition and the like by operating, for example, the second photographing device 2092, independent of the remote control of the critical care technician 121.

(Step S20) The transportation means determination part 307 of the server 3 determines whether the treatment has been completed based on the acquired medical information such as vital checks and the image taken by the photographing device 209. Whether the treatment has been completed may be determined by the critical care technician 121. When it is determined that the treatment has been completed, for example, the transportation means determination part 307 of the server 3 transmits a dispatch stop request to the terminal 6-2 of the ambulance crew 111 via the network NW, and arranges for another transportation means (for example, a taxi). When it is determined that the treatment has not been completed, for example, the robot data control part 302 of the server 3 continues to transmit medical information such as vital checks and environmental data to the terminal 6 while performing control for notification and instruction to continue the treatment until the ambulance arrives according to the remote control.

(Step S21) The terminal 6-1 in the ambulance receives the dispatch stop request. The ambulance crew 111 stops dispatching based on the received result.

(Step S22) The ambulance crew 111 on board the ambulance arrives at the site where the patient is.

(Step S23) The reporter and the like hand over the patient to the ambulance crew. After the patient is handed over, for example, the critical care robot 2 may be returned to the place where it was installed or the like by the reporter, may be self-propelled to return to the place where it was installed or the like by remote control, or may be collected by a recovery vehicle later.

The critical care robot 2 or the server 3 may transmit traffic control information (signals, instructions to surrounding vehicles (particularly effective to automatic driving)) to, for example, a traffic control center or a critical care center, in addition to notifying the ambulance crew of whether they can be dispatched.

In the above-mentioned example, an example in which the reporter goes to pick up the critical care robot 2 has been described, but the disclosure is not limited thereto. For example, the server 3 may, based on the critical care report, notify a person around the critical care robot 2 that is selected to support the movement of the critical care robot 2 to the position where the patient is so that the person around the critical care robot 2 help with the movement.

In this case, the processing of step S14 may be performed as follows. The server 3 may generate route information of the movement route from the selected critical care robot 2 to the reporter (mobile phone 5-2 used by the reporter) in response to the critical care report. Subsequently, the server 3 may generate navigation information from the critical care robot 2 to the reporter by images and audio signals based on the generated route information. Subsequently, the server 3 may transmit the generated route information and navigation information to the critical care robot 2 via the network NW. Subsequently, the critical care robot 2 may notify the received route information and navigation information to a surrounding person to urge the support of movement to the reporter. Then, the critical care robot 2 may navigate from the critical care robot 2 to the reporter based on the route information and the navigation information.

The processing procedure shown in FIG. 24 is an example, and the disclosure is not limited thereto. Several processings may be performed at the same time, or the procedures may be interchanged.

Further, in the above-mentioned example, when the critical care robot 2 performs an instruction or the like by the arms 211 by remote control, the critical care robot 2 takes out the arms 211 from the arm storage part 214 according to the control instruction information of the server 3 to perform the work is performed later, and after the work is completed, the arms 211 are stored in the arm storage part 214.

When the critical care robot 2 performs treatment of a patient, acquisition of medical information such as vital checks, or assistance in response to remote control, the processings of steps S15 and S16 may be performed as follows.

(Step S15) The critical care technician 121 remotely controls the critical care robot 2 to perform treatment on the patient or to use a critical care tool to acquire medical information such as vital checks. The robot data control part 302 of the server 3 generates control instruction information of the arms 211 to make them perform treatment on the patient, or to use a critical care tool to acquire medical information such as vital checks in response to a remote instruction. The robot data control part 302 transmits the generated control instruction information to the critical care robot 2. In addition, the robot data control part 302 may control the arms 211, the pointer 2113, and the like to give a cooperation instruction such as assistance when the patient is treated or when medical information such as vital checks is acquired by using a critical care tool.

(Step S16) When the reporter (or a person around the patient) receives an instruction of cooperation request from the critical care robot 2, according to the instruction of the critical care robot 2, he or she may assist in taking out the critical care tool, and assist in performing treatment or acquiring medical information such as vital checks by using the critical care tool.

The critical care robot 2 or the server 3 may generate traffic control information (signals, instructions to surrounding vehicles (particularly effective to automatic driving)) of the transportation route in addition to the notification of whether the ambulance crew 111 can be dispatched. The critical care robot 2 or the server 3 may transmit the generated traffic control information to, for example, a traffic control center or a critical care center. Thereby, according to the embodiment, it is possible to control the traffic of the transportation route according to the reaction method.

When the critical care robot 2 is remotely controlled, the operation part 603 of the terminal 6-1 used by the critical care technician 121 who performs remote control may be a tactile data glove worn on the operator's hand. The tactile data glove detects the orientation, the movement of each finger, the movement of the hand, and the movement of the arm by the sensor included in the tactile data glove, and transmits the detected operator sensor value to the server 3. The sensor is, for example, an acceleration sensor, a gyroscope sensor, a magnetic force sensor, or the like. The tactile data glove may be provided with a feedback part. The feedback part feeds back the feedback information (pressure, temperature, and the like) from the end effector of the critical care robot 2 to the operator according to the control of the control part 601. Further, the image display part 604 of the terminal 6-1 may be a head-mounted display (HMD). An image taken by the critical care robot 2 is displayed on the HMD. Further, the HMD may be provided with a line-of-sight detector that detects the line-of-sight information of the operator. In this case, the detected line-of-sight information is transmitted to the server 3.

Further, the control part 201 of the critical care robot 2 may estimate the intention of the operation that the operator is trying to perform by inputting the operator sensor value and the line-of-sight information into a trained model. As a result, the control part 201 can realize the work even if the operator does not perform the work accurately, so that the critical care robot 2 can perform the work with high accuracy. In the trained model, for example, the operator sensor value and the line-of-sight information are input in advance, and the work that the operator is trying to perform is learned as teacher data.

As described above, the critical care robot 2 of the embodiment includes the critical care tool storage part 213 which is remotely controllable and which stores critical care tools, and the movement means 212.

As described above, the critical care system 1 of the embodiment includes the photographing device 209 which is capable of remotely controlling at least one of a position and a direction; the critical care tool storage part 213 which stores a critical care tool; the critical care robot 2 which includes at least one end effector which allows for remote control; the terminal 6 with which at least one operator remotely operates the critical care robot; and the server 3 which is capable of acquiring the medical condition information and environmental information acquired by the critical care robot, transmitting the acquired medical condition information and environmental information to the terminal, receiving operation information for the critical care robot from the terminal, and controlling the critical care robot based on the received operation information.

As a result, according to the embodiment, even if there is no person who can perform medical treatment at the site, since the critical care robot can be remotely controlled to acquire the medical condition information, the rescue can be performed. Further, according to the embodiment, since one critical care robot can be remotely controlled smoothly and efficiently by a plurality of operators, rescue can be performed efficiently. Further, according to the embodiment, the doctor can observe the patient from a different viewpoint from the operator of the critical care robot. Further, according to the embodiment, it is possible to select a transportation means from the options in case of an emergency. Further, according to the embodiment, since the transportation method is expanded in addition to the ambulance, ambulances can reach those who really need them. Further, according to the embodiment, the number of times the ambulance is dispatched can be reduced. Further, according to the embodiment, since the instruction to perform privacy protection processing (for example, blurring processing and mosaic processing) is added to the environmental data at the time of storage, it is possible to protect the privacy of the patient, the person who performs treatment on the patient, and the people around the patient.

As described above, the critical care system 1 of the embodiment performs the following processing using the environmental data (site condition, a surrounding person, and the position of the surrounding person) acquired from the critical care robot 2.

I. The control part 201 identifies the position of the target person to be spoken to by the operator (for example, the critical care technician 121), and sets the directivity toward the target person.

II. The support determination part 218 determines whether to request support from another critical care robot in the vicinity, and further outputs the following.

II-1. Audio or image is output to the target person with directivity.

II-2. A support request to another critical care robot in the vicinity is output.

As a result, according to the embodiment, it is possible to ensure the safety of the site and protect the privacy (instruction to put on and take off clothes by a person with the same sex as the patient and the like).

In the above-described embodiment, an example in which one critical care robot 2 gives an instruction, performs treatment, or the like has been described, but the disclosure is not limited thereto. Depending on the condition at the site and the condition of the patient, the critical care robot 2 may transmit a support request to another critical care robot 2 in the vicinity to the server 3 via the network NW. The another critical care robot 2 used for support is remotely controlled by an operator different from the operator of the critical care robot 2 performing the treatment.

As described above, the transportation means determination system 1 of the embodiment includes the critical care robot 2 (critical care device) capable of acquiring the medical condition information and the environmental information; the server 3 which acquires the environmental information and the medical condition information acquired from the critical care device; the terminal 6 capable of acquiring the medical condition information and the environmental information, remotely operating the critical care device, and transmitting a determination result determined based on the acquired medical condition information and the environmental information to the server 3; and the transportation means determination part 307 which determines at least one transportation means from a plurality of transportation means by using at least one information of the medical condition information, the environmental information, and the determination result.

Thereby, according to the embodiment, it is possible to select a transportation means from the options in case of an emergency. Further, according to the embodiment, since the transportation method is expanded in addition to the ambulance, ambulances can reach those who really need them. Further, according to the embodiment, it is possible to request traffic control and perform traffic control according to the transportation means.

Further, the critical care system 1 of the embodiment includes the critical care robot 2 and the critical care reporting device 7 which issues a critical care signal.

Further, the critical care system 1 of the embodiment includes the position information acquisition part (communication part 205, communication part 305) which acquires the position information in which the critical care report is issued; the route generation part (216, 306) which generates a route from the self-position to the site based on the difference of the self-position of the critical care robot 2; and the output part (notification part 207, communication part 305) which notifies surrounding people of navigation from information acquired from the route generation part to the site by sound or image. The critical care robot 2 or the server 3 includes a position information acquisition part and a route generation part.

As a result, according to the embodiment, even if the reporter does not go to pick up the critical care robot 2, the time until the critical care robot 2 arrives can be shortened by having a person near the critical care robot 2 carry it to the position where the patient is.

As described above, the critical care robot 2 of the embodiment includes the photographing device 209 which is remotely controllable and capable of remotely controlling at least one of a position and a direction; the critical care tool storage part 213 which stores critical care tools; and at least one hand 2112 (end effector) which is remotely controllable.

Further, in the critical care robot 2 of the embodiment, the arm 211 includes a pointer 2113.

Further, the critical care robot 2 of the embodiment includes two arms (two arms 211).

Further, the critical care robot 2 of the embodiment includes the photographing device 209 (for example, the second photographing device 2092) which is remotely controllable by a person (for example, a doctor) in addition to the main remote operator (for example, critical care technician 121). The first photographing device 2091 is used, for example, by the critical care technician 121 by remote control.

Further, the critical care robot 2 of the embodiment is equipped with a plurality of directivity notification parts 207 (display device, speaker, and the like).

Further, the critical care robot 2 of the embodiment includes the movement means 212.

Further, the critical care robot 2 of the embodiment is configured so that the arms 211 including its own hand 2112 can be stored in the main body of the critical care robot 2.

As a result, according to the embodiment, the critical care technician 121 can perform rescue by remote control by the remotely controllable critical care robot 2, and the arrival time is shortened; therefore, more lives are saved. Further, according to the embodiment, the number of times the ambulance is dispatched can be reduced; therefore, ambulances can reach the people who really need them.

Modified Example

Figure 25:
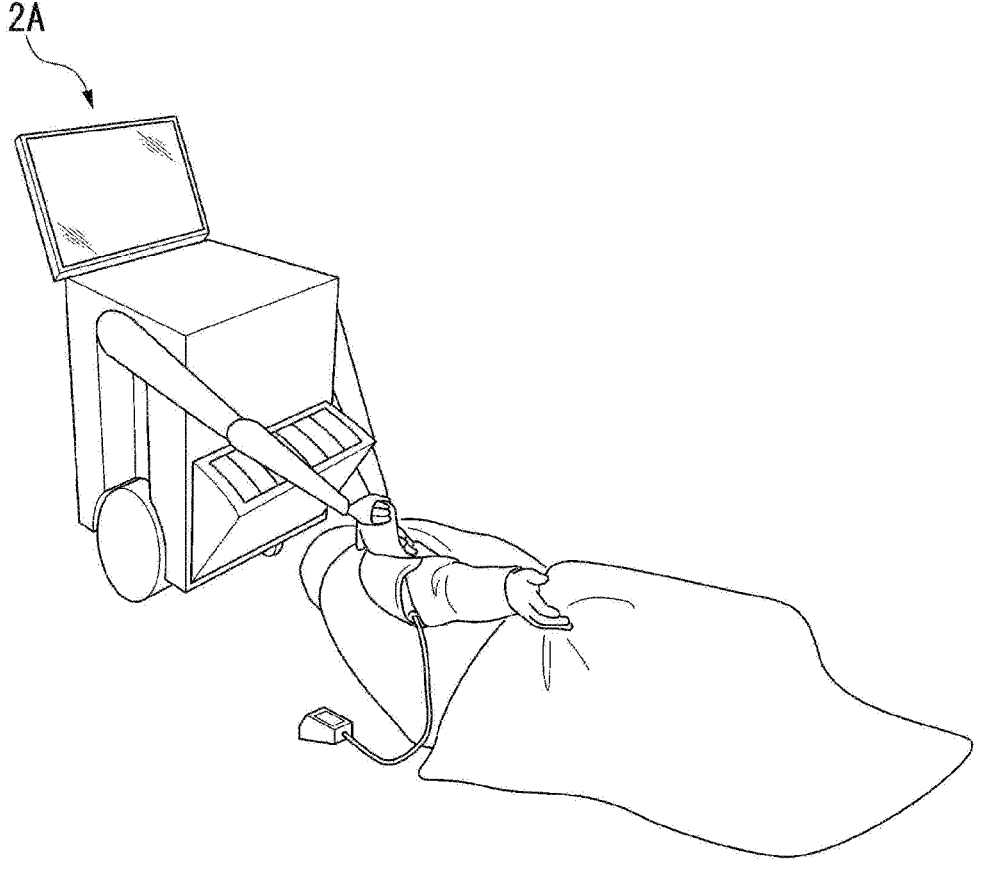
FIG. 25 is a diagram showing an example of a working state at the time of critical care of a critical care robot according to an embodiment which is a modified example.

In this modified embodiment, as shown in FIG. 25, the critical care robot 2A performs treatment on the patient or acquires or assists the medical information such as vital checks according to remote control. FIG. 25 is a diagram showing a processing example of a critical care robot system according to this modified embodiment.

[Configuration Example of Critical Care Robot]

First, a configuration example of the critical care robot 2A will be described.

Figure 26:
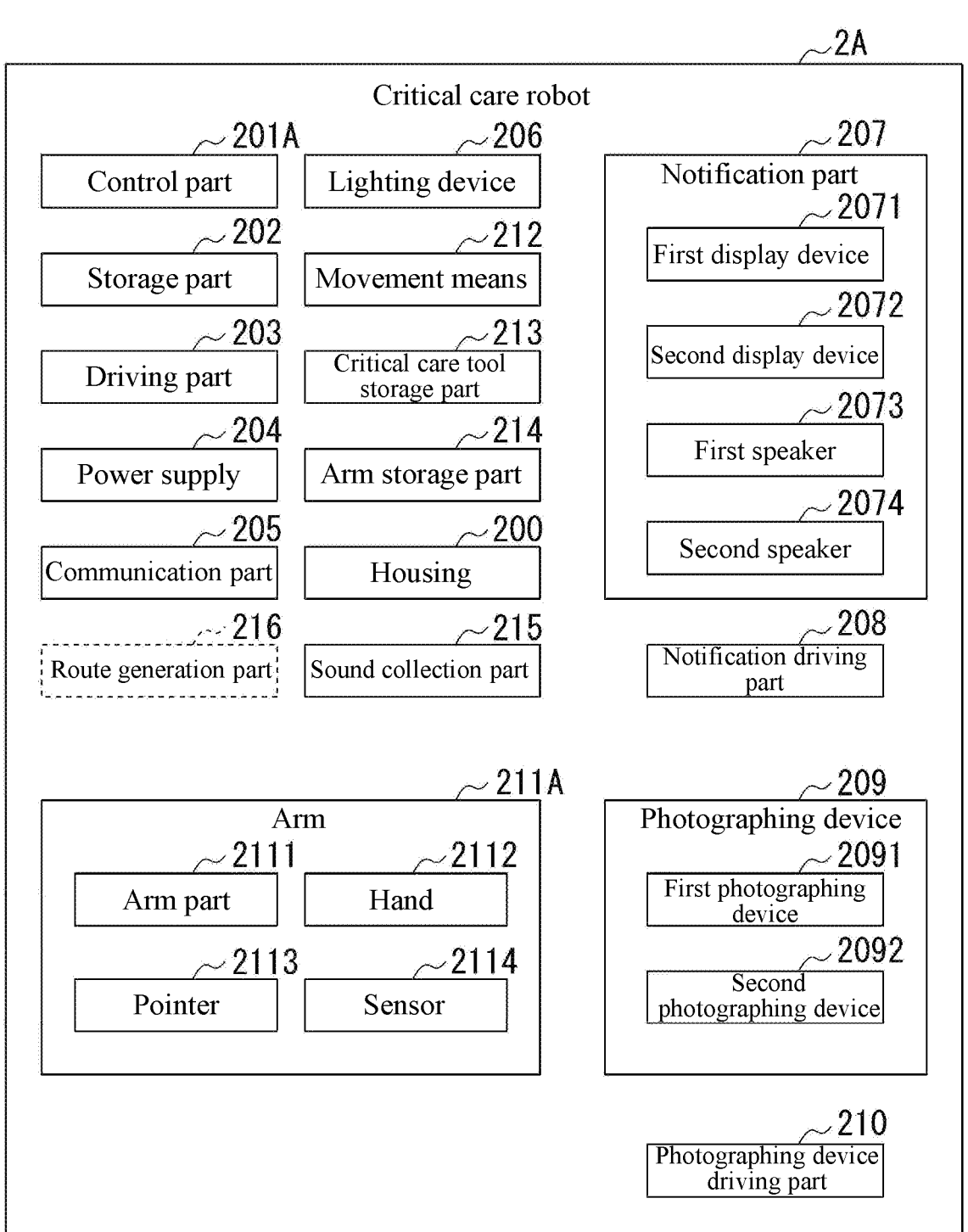
FIG. 26 is a diagram showing a configuration example of a critical care robot according to an embodiment which is a modified example.

FIG. 26 is a diagram showing a configuration example of a critical care robot according to an embodiment. As shown in FIG. 26, the critical care robot 2A includes, for example, a housing 200, a control part 201A, a storage part 202, a driving part 203, a power supply 204, a communication part 205, a lighting device 206, a notification part 207, a notification driving part 208, a photographing device 209, a photographing device driving part 210, arms 211A, a movement means 212, a critical care tool storage part 213, an arm storage part 214, and a sound collection part 215. The critical care robot 2A may include a route generation part 216. The configuration shown in FIG. 8 is an example, and the disclosure is not limited thereto. The critical care robot 2A may be provided with, for example, other functional parts. The critical care robot 2A may be provided with three or more arms 211.

In addition to the operation of the control part 201, the control part 201A controls the operation of the arms 211 of the critical care robot 2A in response to the remote control instruction received from the server 3A by the communication part 205. As a result, in the embodiment, the critical care robot 2A performs the critical care treatments. A plurality of arms 211 may be remotely controlled by different operators (for example, the critical care technician 121 and the assistant critical care technician 123).

The arm 211A is equipped with, for example, a removable cover. The reason for this is that the critical care robot 2A directly touches the patient, the critical care tool, or the like. Therefore, in the critical care robot 2A, a removable cover is attached not only to the arm 211A but also to other parts that may come into direct contact with the patient, the critical care tool, or the like. The cover may be removed or replaced so that an unused cover among multiple layers of covers appears by removing the used cover, and a replacement cover may be included in the critical care tool and may be replaced by a person around the patient. Similar to the first embodiment, such a replacement instruction may be, for example, remotely controlled by the critical care technician 121 to give an instruction to a person around the patient.

When the critical care robot 2A is remotely controlled, the operation part 603 of the terminal 6-1 used by the critical care technician 121 who performs remote control may be a tactile data glove worn on the operator's hand. The tactile data glove detects the orientation, the movement of each finger, the movement of the hand, and the movement of the arm by the sensor included in the tactile data glove, and transmits the detected operator sensor value to the server 3A. The sensor is, for example, an acceleration sensor, a gyroscope sensor, a magnetic force sensor, or the like. The tactile data glove may be provided with a feedback part. The feedback part feeds back the feedback information (pressure, temperature, and the like) from the end effector of the critical care robot 2A to the operator according to the control of the control part 601. Further, the image display part 604 of the terminal 6-1 may be a head-mounted display (HMD). An image taken by the critical care robot 2A is displayed on the HMD. Further, the HMD may be provided with a line-of-sight detector that detects the line-of-sight information of the operator. In this case, the detected line-of-sight information is transmitted to the server 3A.

Further, the control part 201A of the critical care robot 2A may estimate the intention of the operation that the operator is trying to perform by inputting the operator sensor value and the line-of-sight information into a trained model. As a result, the control part 201A can realize the work even if the operator does not perform the work accurately, so that the critical care robot 2A can perform the work with high accuracy. In the trained model, for example, the operator sensor value and the line-of-sight information are input in advance, and the work that the operator is trying to perform is learned as teacher data.

[Configuration Example of Server]

Next, a configuration example of the server 3A will be described.

Figure 27:
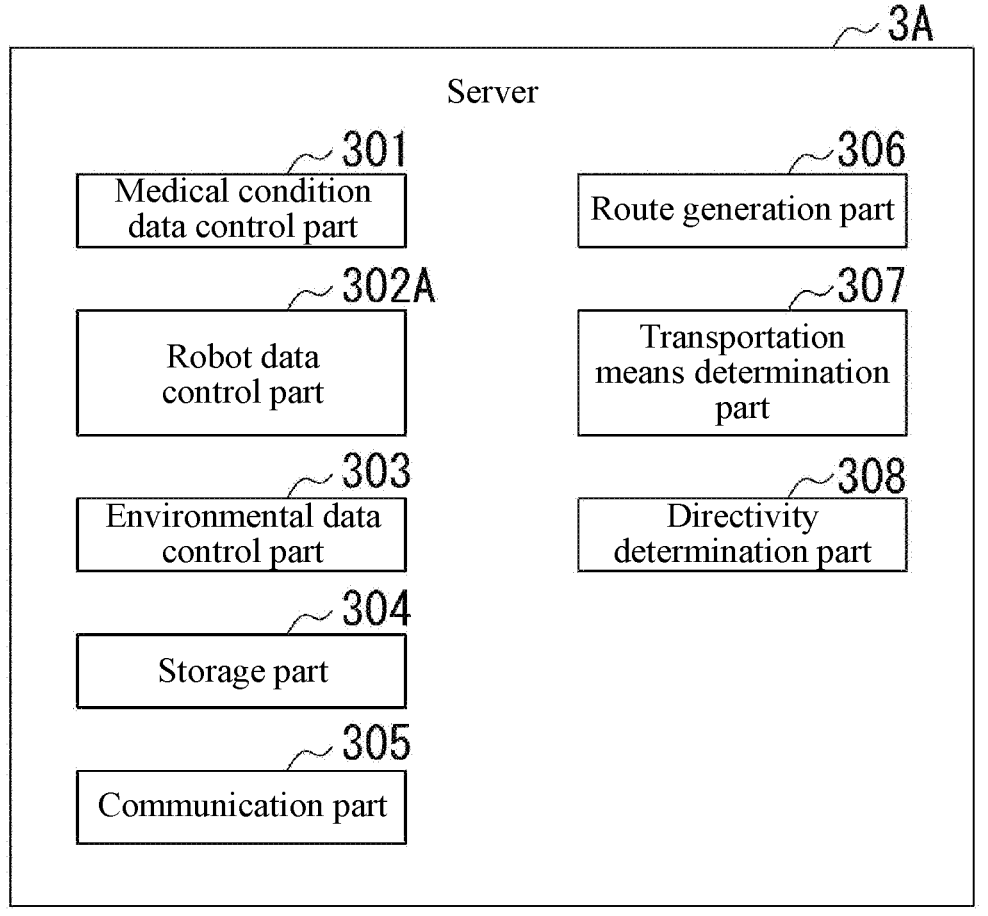
FIG. 27 is a diagram showing a configuration example of a server according to an embodiment which is a modified example.

FIG. 27 is a diagram showing a configuration example of a server according to an embodiment. As shown in FIG. 27, the server 3A includes, for example, a medical condition data control part 301, a robot data control part 302A, an environmental data control part 303, a storage part 304, a communication part 305, a route generation part 306, a transportation means determination part 307, and a directivity determination part 308. The configuration shown in FIG. 27 is an example, and the disclosure is not limited thereto.

In addition to the operation of the robot data control part 302, the robot data control part 302A generates control instruction information so as to operate the arms 211A of the critical care robot 2A to treat the patient or to use a critical care tool to acquire medical information such as vital checks based on the remote control of critical care technician 121. The robot data control part 302A transmits the generated control instruction information to the critical care robot 2A.

[Processing Example of Critical Care Robot System 1A]

Figure 28:
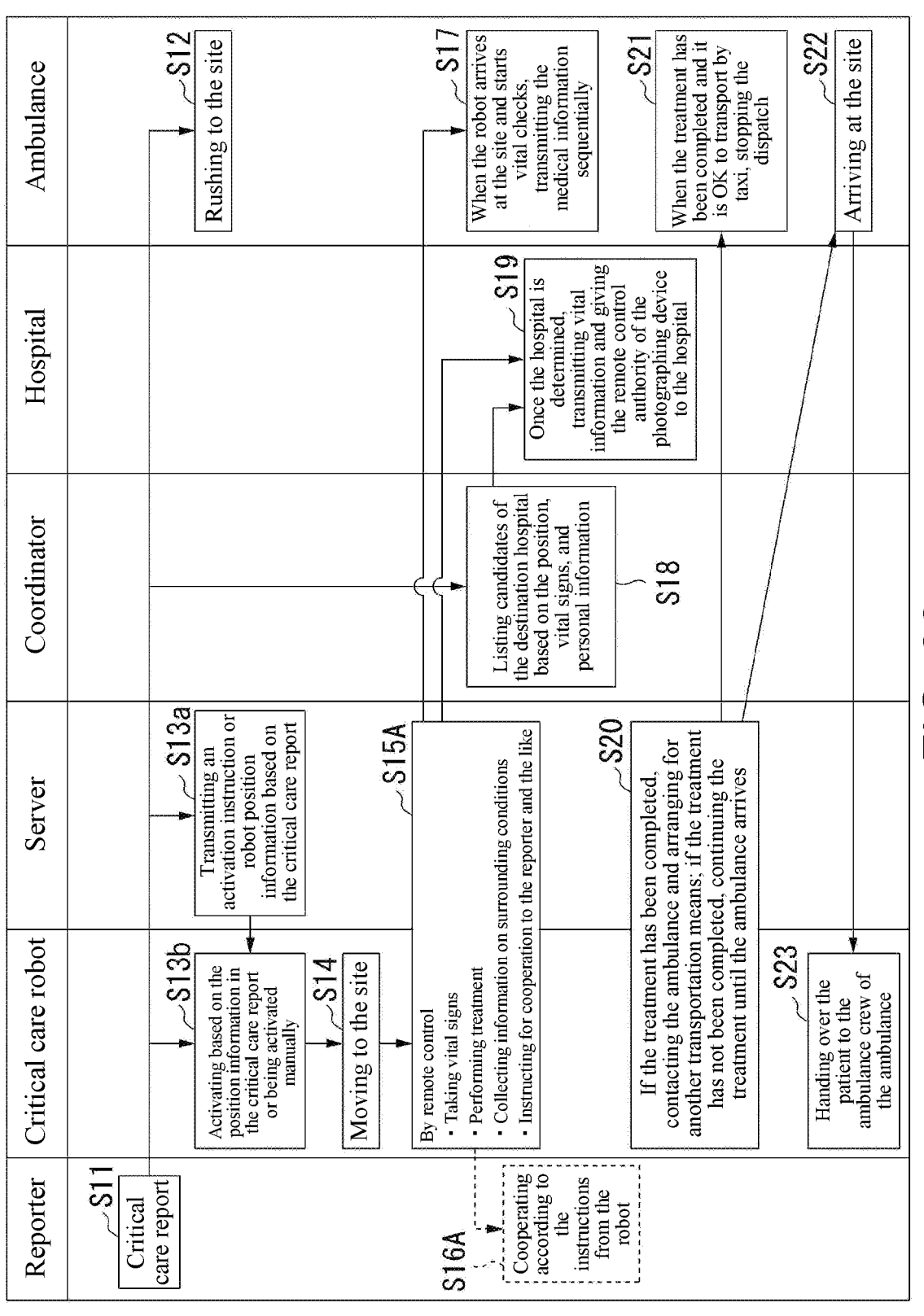
FIG. 28 is a diagram showing a processing example of a critical care robot system according to an embodiment which is a modified example.

Next, a processing example of the critical care robot system 1A of the embodiment will be described with reference to FIGS. 3 and 25 to 28. FIG. 28 is a diagram showing a processing example of a critical care robot system according to this embodiment. In addition, in FIG. 28, the "critical care robot" is also referred to as the "robot."

(Step S15A) After step S14, the critical care technician 121 remotely controls the critical care robot 2A to perform treatment on the patient or to use a critical care tool to acquire medical information such as vital checks. The robot data control part 302A of the server 3A generates control instruction information of the arms 211A to make them perform treatment on the patient, or to use a critical care tool to acquire medical information such as vital checks in response to a remote instruction. The robot data control part 302A transmits the generated control instruction information to the critical care robot 2A. In addition, the robot data control part 302A may control the arms 211A, the pointer 2113, and the like to give a cooperation instruction such as assistance when the patient is treated or when medical information such as vital checks is acquired by using a critical care tool.

(Step S16A) When the reporter (or a person around the patient) receives an instruction of cooperation request from the critical care robot 2A, according to the instruction of the critical care robot 2A, he or she may assist in taking out the critical care tool, and assist in performing treatment or acquiring medical information such as vital checks by using the critical care tool.

The processing procedure shown in FIG. 10 is an example, and the disclosure is not limited thereto. Several processings may be performed at the same time, or the procedures may be interchanged.

As described above, in the critical care robot 2A of the embodiment, in addition to the critical care robot 2, a hand 2112 (end effector) capable of operating the critical care tool is connected to the arm 211A.

As a result, according to the embodiment, by remote control, the critical care technician 121 or the like can perform treatment on the patient or use a critical care tool to acquire medical information such as vital checks.

In the above-described embodiment, an example in which one critical care robot 2 (or 2A) gives an instruction, performs treatment, or the like has been described, but the disclosure is not limited thereto. Depending on the condition at the site and the condition of the patient, the critical care robot 2 (or 2A) may transmit a support request to another critical care robot 2 (or 2A) in the vicinity to the server 3 (or 3A) via the network NW. The another critical care robot 2 (or 2A) used for support is remotely controlled by an operator different from the operator of the critical care robot 2 (or 2A) performing the treatment.

A program for realizing all or part of the functions of the components of the critical care robot 2 (or 2A), the server 3 (or 3A), and the terminal 6 in the disclosure is recorded on a computer-readable recording medium, and the program recorded in this recording medium may be read into a computer system and executed to perform all or part of the processing performed by the critical care robot 2, the server 3, and the terminal 6. The term "computer system" as used herein includes an OS and hardware such as peripheral devices. In addition, the "computer system" includes a system built on a local network, a system built on the cloud, and the like. Further, the "computer-readable recording medium" refers to a portable medium such as a flexible disk, a magneto-optical disk, a ROM, or a CD-ROM, and a storage device such as a hard disk built in a computer system. Furthermore, a "computer-readable recording medium" includes a medium that holds a program for a certain period of time, such as a volatile memory (RAM) inside a computer system that serves as a server or client when a program is transmitted via a network such as the Internet or a communication line such as a telephone line.

Further, the program may be transmitted from a computer system in which this program is stored in a storage device or the like to another computer system via a transmission medium or by a transmission wave in the transmission medium. Here, the "transmission medium" for transmitting a program refers to a medium having a function of transmitting information, such as a network (communication network) like the Internet or a communication line like a telephone line. Further, the above program may be for realizing a part of the above-mentioned functions. Further, it may be a so-called difference file (difference program) that can realize the above-mentioned function in combination with a program already recorded in the computer system.

Although embodiments for implementing the disclosure have been described above by the embodiments, the disclosure is not limited to these embodiments, and various modifications and replacements may be added without departing from the spirit of the disclosure.

What is claimed is:

1. A critical care system comprising:
a first photographing device which is capable of remotely controlling at least one of a position and a direction;
a critical care tool storage part which stores a critical care tool;
a critical care robot which comprises at least one end effector that allows for remote control, wherein the at least one end effector comprises a pointer, and wherein the pointer instructs a person who performs a treatment on a patient to be treated by the remote control;
a terminal with which at least one operator remotely operates the critical care robot; and
a server which is capable of acquiring medical condition information and environmental information acquired by the critical care robot, transmitting the acquired medical condition information and environmental information to the terminal, receiving operation information for the critical care robot from the terminal, and controlling the critical care robot based on the received operation information.

2. The critical care system according to claim 1, wherein the critical care robot is capable of being operated by a plurality of people, and
the server transfers a control right of an operator having a low priority to an operator having a high priority based on a priority.

3. The critical care system according to claim 1, wherein there are a plurality of the terminals, a first terminal is operated by an operator of the critical care robot, and a second terminal is operated by a doctor,
the critical care robot comprises a second photographing device, and
the second photographing device is operable by the doctor by operating the second terminal, and is capable of observing a patient from a different viewpoint from the operator of the critical care robot.

4. The critical care system according to claim 1, wherein there are a plurality of the terminals, and a coordinator operates another terminal different from a terminal operated by an operator of the critical care robot, and
the another terminal transmits a result of determining a destination hospital based on medical condition information and environmental data by the coordinator to the server.

5. The critical care system according to claim 1, wherein the server:
transmits the medical condition information acquired by the critical care robot to the terminal in real time, and
adds a processing instruction to environmental data acquired by the critical care robot at the time of storage for privacy protection.

6. A critical care system control method for a critical care system, the critical care system comprising a first photographing device which is capable of remotely controlling at least one of a position and a direction, a critical care tool storage part which stores a critical care tool, a critical care robot which comprises at least one end effector that allows for remote control, a terminal with which at least one operator remotely operates the critical care robot, and a server,
wherein the at least one end effector of the critical care robot comprises a pointer,
wherein the critical care system control method comprises:
acquiring, by the critical care robot, medical condition information and environmental information, and transmitting the acquired medical condition information and environmental information to the server; and
transmitting, by the server, the acquired medical condition information and environmental information to the terminal, receiving operation information for the critical care robot from the terminal, and controlling the critical care robot based on the received operation information to use the pointer to instruct a person who performs a treatment on a patient to be treated by the remote control.

7. A non-transitory computer-readable recording medium recording a program for a critical care system, the critical care system comprising a first photographing device capable of remotely controlling at least one of a position and a direction, a critical care tool storage part which stores a critical care tool, a critical care robot which comprises at least one end effector that allows for remote control, a terminal with which at least one operator remotely operates the critical care robot, and a server,
wherein the at least one end effector of the critical care robot comprises a pointer,
wherein the program causes a computer of the server to:
acquire, by the critical care robot, medical condition information and environmental information, and transmit the acquired medical condition information and environmental information to the server;
transmit the acquired medical condition information and the environmental information to the terminal; and
receive operation information for the critical care robot from the terminal, and control the critical care robot based on the received operation information to use the pointer to instruct a person who performs a treatment on a patient to be treated by the remote control.

8. A critical care robot which allows for remote control, the critical care robot comprising:
a first photographing device which is capable of remotely controlling at least one of a position and a direction through a remote control of a main remote operator by using a terminal via a server;
a critical care tool storage part which stores a critical care tool; and
at least one end effector which allows for remote control and comprises a pointer, wherein the pointer instructs a person who performs a treatment on a patient to be treated by the remote control; and
a communication part that transmits medical condition information and environmental information to the terminal via the server, and receive operation information for controlling the critical care robot from the terminal via the server.

9. The critical care robot according to claim 8, further comprising two arms, wherein the end effector is capable of operating the critical care tool and is connected to the two arms.

10. The critical care robot according to claim 8, further comprising a second photographing device which is connectable by another person in addition to a main remote operator.

11. The critical care robot according to claim 8, further comprising a plurality of display devices and speakers with directivity.

12. The critical care robot according to claim 8, further comprising a movement means.

13. The critical care robot according to claim 12, wherein the movement means is driven to assist movement when the critical care robot is moving.

14. The critical care robot according to claim 8, wherein the end effector is storable in a main body.

15. A critical care robot system comprising:

the critical care robot according to claim 8;

at least one terminal used for remote control of the critical care robot;

a position information acquisition device which acquires position information of a patient to receive critical care; and a server which generates control information for the critical care robot based on remote control from the terminal.

\* \* \* \* \*